US010206570B2

(12) United States Patent
McKenna et al.

(10) Patent No.: US 10,206,570 B2
(45) Date of Patent: Feb. 19, 2019

(54) ADAPTIVE WIRELESS BODY NETWORKS

(75) Inventors: Edward M. McKenna, Boulder, CO (US); Daniel Lisogurski, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 1354 days.

(21) Appl. No.: 12/714,532

(22) Filed: Feb. 28, 2010

(65) Prior Publication Data

US 2011/0213216 A1 Sep. 1, 2011

(51) Int. Cl.
*A61B 5/00* (2006.01)
*H04W 52/02* (2009.01)

(52) U.S. Cl.
CPC .... *A61B 5/0002* (2013.01); *A61B 2560/0209* (2013.01); *G06F 1/3203* (2013.01); *H04W 52/02* (2013.01); *Y02D 70/10* (2018.01); *Y02D 70/14* (2018.01); *Y02D 70/142* (2018.01); *Y02D 70/144* (2018.01); *Y02D 70/162* (2018.01); *Y02D 70/22* (2018.01)

(58) Field of Classification Search
USPC .................................................. 600/300–301
See application file for complete search history.

(56) References Cited

U.S. PATENT DOCUMENTS

| 6,398,727 | B1 | 6/2002 | Bui et al. |
| 6,579,242 | B2 | 6/2003 | Bui et al. |
| 6,792,396 | B2 | 9/2004 | Inda et al. |
| 6,830,549 | B2 | 12/2004 | Bui et al. |
| 6,840,904 | B2 | 1/2005 | Goldberg |
| 6,934,571 | B2 | 8/2005 | Wiesmann et al. |
| 7,001,334 | B2 | 2/2006 | Reed et al. |

(Continued)

FOREIGN PATENT DOCUMENTS

| JP | 2006320731 A | 11/2006 |
| JP | 2006320732 A | 11/2006 |

(Continued)

OTHER PUBLICATIONS

Cymbet EnerChip Energy Harvesting Module Wins Best of Sensors Expo 2009 Award; Nanowerk News; http://www.nanowerk.com/news/newsid=11103.php.

(Continued)

*Primary Examiner* — Christopher A Flory
*Assistant Examiner* — Shirley Jian
(74) *Attorney, Agent, or Firm* — Fletcher Yoder PC

(57) ABSTRACT

Systems, methods, and devices for obtaining physiological measurements of a patient using an adaptive body network are provided. In one example, a wireless medical sensor may include physiological sensor circuitry, wireless transceiver circuitry, and control circuitry. The physiological sensor circuitry may be capable of obtaining a physiological measurement of a patient. The wireless transceiver circuitry may be capable of joining a wireless web that includes at least one other wireless medical sensor, through which the wireless transceiver circuitry may communicate the physiological measurement to an external device. The control circuitry may be capable of determining a data update rate at which to operate the physiological sensor or the wireless transceiver circuitry, or a combination thereof, based at least in part on a status of the patient.

31 Claims, 13 Drawing Sheets

(56) References Cited

U.S. PATENT DOCUMENTS

| | | | |
|---|---|---|---|
| 7,142,123 B1* | 11/2006 | Kates | G01N 27/048 340/602 |
| 7,161,484 B2 | 1/2007 | Tsoukalis | |
| 7,215,991 B2 | 5/2007 | Besson et al. | |
| 7,256,695 B2* | 8/2007 | Hamel et al. | 340/572.1 |
| 7,387,607 B2 | 6/2008 | Holt et al. | |
| 7,396,330 B2 | 7/2008 | Banet et al. | |
| 7,448,996 B2 | 11/2008 | Khanuja et al. | |
| 7,481,772 B2 | 1/2009 | Banet | |
| 7,486,977 B2 | 2/2009 | Sweitzer et al. | |
| 7,498,953 B2* | 3/2009 | Salser, Jr. | H04Q 9/00 340/636.1 |
| 7,499,739 B2 | 3/2009 | Sweitzer et al. | |
| 7,555,517 B2 | 6/2009 | Kreiner et al. | |
| 7,598,878 B2 | 10/2009 | Goldreich | |
| 7,729,733 B2 | 6/2010 | Al-Ali et al. | |
| 7,747,301 B2 | 6/2010 | Cheng et al. | |
| 7,949,404 B2* | 5/2011 | Hill | 607/60 |
| 8,926,509 B2* | 1/2015 | Magar et al. | 600/301 |
| 2001/0051787 A1* | 12/2001 | Haller | A61B 5/0031 604/66 |
| 2005/0113655 A1 | 5/2005 | Hull | |
| 2005/0119533 A1 | 6/2005 | Sparks et al. | |
| 2005/0135288 A1 | 6/2005 | Al-Ali | |
| 2005/0228300 A1 | 10/2005 | Jaime et al. | |
| 2005/0245831 A1 | 11/2005 | Banet | |
| 2005/0261598 A1 | 11/2005 | Banet et al. | |
| 2005/0273013 A1 | 12/2005 | Kent | |
| 2005/0275527 A1* | 12/2005 | Kates | G08B 1/08 340/539.22 |
| 2005/0275528 A1* | 12/2005 | Kates | G08B 1/08 340/539.22 |
| 2005/0275529 A1* | 12/2005 | Kates | G08B 1/08 340/539.22 |
| 2005/0275530 A1* | 12/2005 | Kates | G08B 1/08 340/539.22 |
| 2005/0280531 A1 | 12/2005 | Fadem et al. | |
| 2006/0009698 A1 | 1/2006 | Banet et al. | |
| 2006/0020216 A1 | 1/2006 | Oishi et al. | |
| 2006/0069319 A1 | 3/2006 | Elhag et al. | |
| 2006/0079794 A1 | 4/2006 | Liu et al. | |
| 2006/0094426 A1 | 5/2006 | Donaho et al. | |
| 2006/0098666 A1 | 5/2006 | Francis Conde Powell | |
| 2006/0116557 A1* | 6/2006 | Moore et al. | 600/300 |
| 2006/0122466 A1 | 6/2006 | Nguyen-Dobinsky et al. | |
| 2006/0142648 A1 | 6/2006 | Banet et al. | |
| 2006/0253010 A1 | 11/2006 | Brady et al. | |
| 2006/0273896 A1* | 12/2006 | Kates | G08B 21/0236 340/539.18 |
| 2006/0278222 A1 | 12/2006 | Schermeier et al. | |
| 2007/0004971 A1 | 1/2007 | Riley et al. | |
| 2007/0018832 A1* | 1/2007 | Beigel | G06K 19/07345 340/572.7 |
| 2007/0073119 A1 | 3/2007 | Wobermin et al. | |
| 2007/0073558 A1 | 3/2007 | Hall et al. | |
| 2007/0100213 A1 | 5/2007 | Dossas et al. | |
| 2007/0106132 A1 | 5/2007 | Elhag et al. | |
| 2007/0135866 A1 | 6/2007 | Baker et al. | |
| 2007/0142715 A1 | 6/2007 | Banet et al. | |
| 2007/0150014 A1 | 6/2007 | Kramer et al. | |
| 2007/0156450 A1 | 7/2007 | Roehm et al. | |
| 2007/0173701 A1 | 7/2007 | Al-Ali | |
| 2007/0197878 A1* | 8/2007 | Shklarski | 600/300 |
| 2007/0197881 A1* | 8/2007 | Wolf et al. | 600/300 |
| 2007/0208235 A1 | 9/2007 | Besson et al. | |
| 2007/0255116 A1* | 11/2007 | Mehta et al. | 600/300 |
| 2007/0258395 A1* | 11/2007 | Jollota et al. | 370/310 |
| 2007/0282177 A1 | 12/2007 | Pilz | |
| 2008/0021287 A1* | 1/2008 | Woellenstein et al. | 600/300 |
| 2008/0097178 A1 | 4/2008 | Banet et al. | |
| 2008/0146890 A1 | 6/2008 | LeBoeuf et al. | |
| 2008/0171311 A1 | 7/2008 | Centen et al. | |
| 2008/0191866 A1 | 8/2008 | Falck et al. | |
| 2008/0194925 A1 | 8/2008 | Alsafadi et al. | |
| 2008/0208009 A1 | 8/2008 | Shklarski | |
| 2008/0215120 A1 | 9/2008 | Dicks et al. | |
| 2008/0215360 A1 | 9/2008 | Dicks et al. | |
| 2008/0222251 A1 | 9/2008 | Parthasarathy | |
| 2008/0228045 A1 | 9/2008 | Gao et al. | |
| 2008/0281168 A1 | 11/2008 | Gibson et al. | |
| 2009/0054737 A1* | 2/2009 | Magar et al. | 600/300 |
| 2009/0063193 A1* | 3/2009 | Barton et al. | 705/3 |
| 2009/0069642 A1* | 3/2009 | Gao | A61B 5/02055 600/300 |
| 2009/0105549 A1* | 4/2009 | Smith et al. | 600/300 |
| 2009/0192362 A1* | 7/2009 | Sweeney | 600/300 |
| 2009/0203971 A1* | 8/2009 | Sciarappa | G08B 21/0453 600/301 |
| 2009/0318779 A1* | 12/2009 | Tran | 600/301 |
| 2010/0094098 A1* | 4/2010 | Smith et al. | 600/300 |
| 2010/0137693 A1* | 6/2010 | Porras et al. | 600/301 |
| 2010/0217099 A1* | 8/2010 | LeBoeuf et al. | 600/301 |
| 2010/0274100 A1* | 10/2010 | Behar et al. | 600/301 |
| 2011/0034783 A1* | 2/2011 | Lisogurski et al. | 600/301 |
| 2011/0068921 A1* | 3/2011 | Shafer | 340/571 |
| 2011/0213217 A1* | 9/2011 | McKenna | A61B 5/14552 600/301 |
| 2011/0288379 A1* | 11/2011 | Wu | 600/301 |
| 2014/0206948 A1* | 7/2014 | Romem | A61B 5/0022 600/301 |

FOREIGN PATENT DOCUMENTS

| | | |
|---|---|---|
| WO | WO 2004/084720 A2 | 10/2004 |
| WO | WO 2005/114524 A2 | 12/2005 |
| WO | WO 2005/122879 A1 | 12/2005 |
| WO | WO 2006/006107 A1 | 1/2006 |
| WO | WO 2006/009830 A2 | 1/2006 |
| WO | WO 2006/039752 A1 | 4/2006 |
| WO | WO 2006/048840 A1 | 5/2006 |
| WO | WO 2006/051464 A1 | 5/2006 |
| WO | WO 2006/064397 A2 | 6/2006 |
| WO | WO 2007/013054 A1 | 2/2007 |
| WO | WO 2007/017777 A2 | 2/2007 |
| WO | WO 2007/070855 A2 | 6/2007 |
| WO | WO 2007/071180 A1 | 6/2007 |
| WO | WO 2008/073584 A2 | 6/2008 |
| WO | WO 2008/096241 A2 | 8/2008 |

OTHER PUBLICATIONS

Michael Koplow et al.; Thick film thermoelectric energy harvesting systems for biomedical applications; Department of Mechanical Engineering, UC Berkeley, Berkeley, CA 94720-1760; Department of Materials Science and Engineering, UC Berkeley, Berkeley, CA 94720-1760; Corresponding author: mkoplow@berkeley.edu; (undated).

* cited by examiner

ADAPTIVE WIRELESS BODY NETWORKS

BACKGROUND

The present disclosure relates generally to medical sensors and, more particularly, to adaptive networks of wireless medical sensors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In certain medical settings, many medical sensors may monitor a patient. Such sensors may include, for example, photoplethysmographic sensors, temperature sensors, respiration bands, blood pressure sensors, electrocardiogram (ECG) sensors, electroencephalogram (EEG) sensors, pulse transit time sensors, and so forth. These medical sensors generally may communicate with a local patient monitor or a network using a communication cable. However, the use of communication cables may limit the range of applications available, as the cables may become prohibitively expensive at long distances and may physically tether a patient to a monitoring device, thereby limiting the patient's range of motion. Though wireless medical sensors may transmit information without need of a communication cable, many wireless medical sensors may employ large batteries that are cumbersome, uncomfortable to wear, and expensive.

SUMMARY

Certain aspects commensurate in scope with the originally claimed embodiments are set forth below. It should be understood that these aspects are presented merely to provide the reader with a brief summary of certain forms the embodiments might take and that these aspects are not intended to limit the scope of the presently disclosed subject matter. Indeed, the embodiments may encompass a variety of aspects that may not be set forth below.

Present embodiments relate to systems, methods, and devices for obtaining physiological measurements of a patient using an adaptive body network. In one example, a wireless medical sensor may include physiological sensor circuitry, wireless transceiver circuitry, and control circuitry. The physiological sensor circuit may be capable of obtaining a physiological measurement of a patient. The wireless transceiver circuitry may be capable of joining a wireless web that includes at least one other wireless medical sensor, through which the wireless transceiver circuitry may communicate the physiological measurement to an external device. The control circuitry may be capable of determining a data update rate at which to operate the physiological sensor or the wireless transceiver circuitry, or a combination thereof, based at least in part on a status of the patient.

BRIEF DESCRIPTION OF THE DRAWINGS

Advantages of the presently disclosed subject matter may become apparent upon reading the following detailed description and upon reference to the drawings in which.

DETAILED DESCRIPTION

Figure 1:
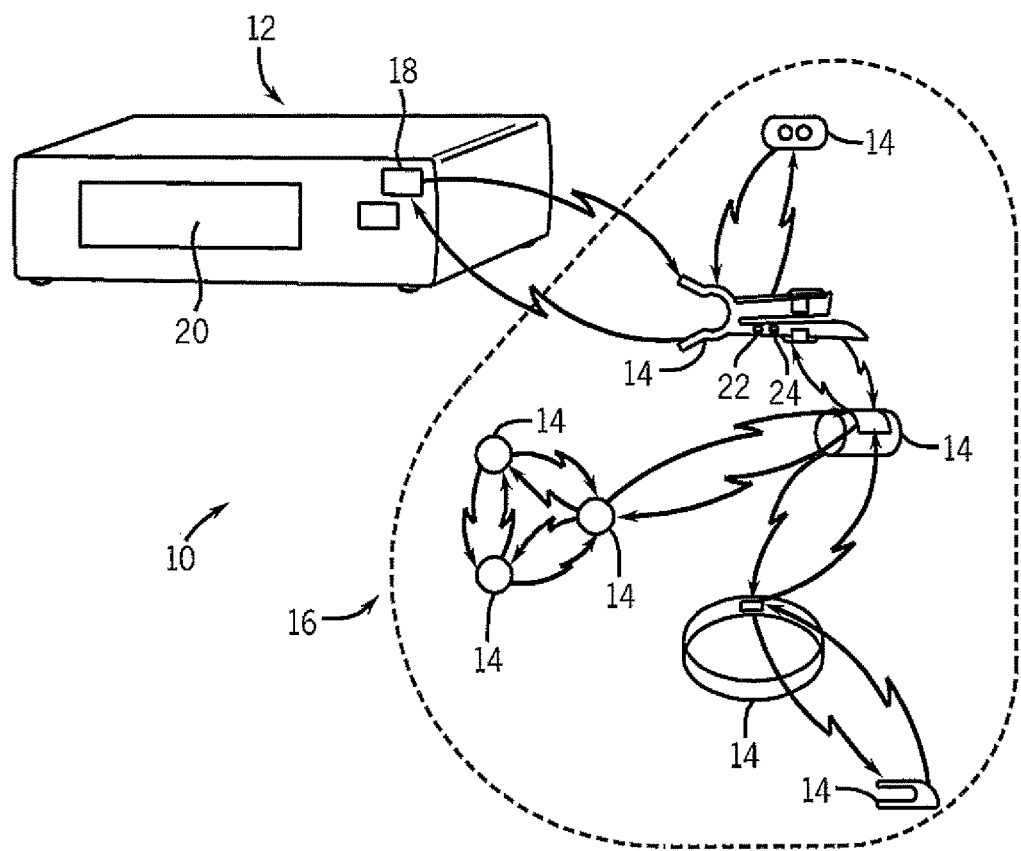
FIG. 1 is a perspective view of a wireless web medical sensor system, in accordance with an embodiment.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Embodiments of the present disclosure may apply to a variety of medical sensors, including photoplethysmographic sensors, temperature sensors, respiration bands, blood pressure sensors, electrocardiogram (ECG) sensors, electroencephalogram (EEG) sensors, pulse transit time sensors, and so forth. These sensors may obtain a variety of physiological measurements based on information detected from patient tissue. Certain medical events may call for monitoring many physiological parameters of a patient using many different medical sensors. Under such conditions, in accordance with embodiments of the present disclosure, many low-power medical sensors may communicate wirelessly with one another to form a wireless web of medical sensors. By forming a wireless web (e.g., a wireless personal area network (WPAN) and/or wireless mesh network of devices) through which to communicate, the medical sensors may conserve power. These low-power wireless medical sensors may be powered by relatively unobtrusive batteries and/or using various energy harvesting techniques, such as piezoelectric energy harvesting, inductive energy harvesting, and/or thermoelectric energy harvesting.

A wireless web of medical sensors, such as those disclosed herein, may efficiently obtain and communicate physiological parameters from a patient to a patient monitor. Specifically, the medical sensors of the wireless web may determine, based on any suitable number of factors, which of the medical sensors should communicate with the patient monitor. In some embodiments, the primary factor of this determination may be the proximity of a given medical sensor to the patient monitor.

Additionally or alternatively, the medical sensors of the wireless web may determine a suitable data update rate level for their operation based on patient physiology and/or other factors. Thus, when measured patient parameters indicate that the patient is healthy, the medical sensor data update rate level may be relatively low, conserving power. In contrast, when the measured patient parameters indicate the patient is suffering a condition or complication, the medical sensor data update rate level may be relatively higher, enabling medical personnel to more closely observe the patient. In some embodiments, the patient monitor may assess these one or more factors to determine the medical sensor data update rate level. The patient monitor may thereafter communicate the determined data update rate level to the wireless web of medical sensors.

With the foregoing in mind, FIG. 1 is a perspective view of a medical sensor system 10 including a patient monitor 12 for use with a wireless web of medical sensors 14. By way of example, embodiments of the system 10 may be implemented with any suitable medical sensors 14 and patient monitor 12, such as those available from Nellcor Puritan Bennett LLC. The medical sensor system 10 may determine a variety of physiological parameters of a patient based on wireless signals received from the medical sensors 14. As illustrated in FIG. 1, the medical sensor system 10 may function with any suitable wireless medical sensors 14 capable of joining a wireless web 16, which may include, for example, photoplethysmographic sensors, temperature sensors, respiration bands, blood pressure sensors, electrocardiogram (ECG) sensors, electroencephalogram (EEG) sensors, pulse transit time sensors, and so forth. Generally, the medical sensors 14 may be relatively low-power devices that receive power from batteries and/or various energy harvesting techniques. Such energy harvesting techniques may include, for example, piezoelectric energy harvesting, inductive energy harvesting, and/or thermoelectric energy harvesting. Certain embodiments of medical sensors 14 that employ such energy harvesting techniques are described below.

The patient monitor 12 may communicate with the wireless web 16 of medical sensors 14 via a wireless module 18. The wireless module 18 may enable the patient monitor to send and receive wireless communication with the wireless web 16 of medical sensors 14 using any suitable wireless protocol. For example, the wireless module 18 may communicate using the IEEE 802.15.4 standard, which may include, for example, ZigBee, WirelessHART, and/or MiWi. Additionally or alternatively, the wireless module 18 may communicate using the Bluetooth standard or one or more of the IEEE 802.11.x standards. In some embodiments, the wireless module 18 may be capable of optical communication, such as free space optics (FSO), using light emitting diodes (LEDs) and/or laser diodes (LDs). The patient monitor 12 may include a display 20, memory, a processor, and various monitoring and control features. Based on sensor data received from the wireless web 16 of medical sensors 14, the patient monitor 12 may display patient parameters and perform various additional algorithms. Among other things, the patient monitor 12 may process the sensor data to determine a status of the patient and, depending on the status, may indicate a data update rate level at which the medical sensors 14 should operate.

In the presently illustrated embodiment of FIG. 1, the medical sensors 14 may include any suitable wireless sensors capable of joining the wireless web 16. The medical sensors 14 may include photoplethysmographic sensors for placement on various patient body locations, temperature sensors, respiration bands, blood pressure sensors, ECG sensors, EEG sensors, and/or pulse transit time sensors, and so forth. The medical sensors 14 may attach to patient tissue (e.g., a patient's finger, ear, forehead, chest, or toe). By way of example, one of the medical sensors 14 may be a photoplethysmographic sensor that includes an emitter 22 and a detector 24. When attached to pulsatile patient tissue, the emitter 22 may emit light at certain wavelengths into the tissue and the detector 24 may receive the light after it has passed through or has been reflected by the tissue. For example, the emitter 22 may emit light from two or more light emitting diodes (LEDs) or other suitable light sources into the pulsatile tissue. The reflected or transmitted light may be detected by the detector 24, which may be, for example, a photodiode or photo-detector. The amount of light that passes through the tissue, as well as other characteristics of the light, may vary in accordance with the changing amount of certain blood constituents in the tissue and the related light absorption and/or scattering.

Each of the medical sensors 14 may include wireless communication capabilities to enable communication with other wireless medical sensors 14 via such wireless protocols as relate to the IEEE 802.15.4 standard, which may include, for example, ZigBee, WirelessHART, and/or MiWi. Additionally or alternatively, the wireless module 18 may be capable of communicating using the Bluetooth standard or one or more of the IEEE 802.11.x standards. In some embodiments, the wireless module 18 may involve optical communication, such as free space optics (FSO), using light emitting diodes (LEDs) and/or laser diodes (LDs). The sensors 14 may self-assemble into the wireless web 16 by communicating with one another. Based on any suitable factors, the medical sensors 14 may select one of the medical sensors 14 of the wireless web 16 to serve as a main communication point with the patient monitor 12.

To conserve power, the medical sensors 14 may operate various data update rate levels depending on the status of the patient. When the patient is healthy, the medical sensors 14 may gather fewer physiological measurements and/or conduct such measurements only occasionally through the wireless web 16 to the patient monitor 12. When the patient suffers from an identified condition or disease, the medical sensors 14 may gather more physiological measurements and/or conduct such measurements more quickly through the wireless web 16 to the patient monitor 12. Techniques related to determining the data update rate level at which to operate are discussed below with reference to FIGS. 11 and 12.

Figure 2:
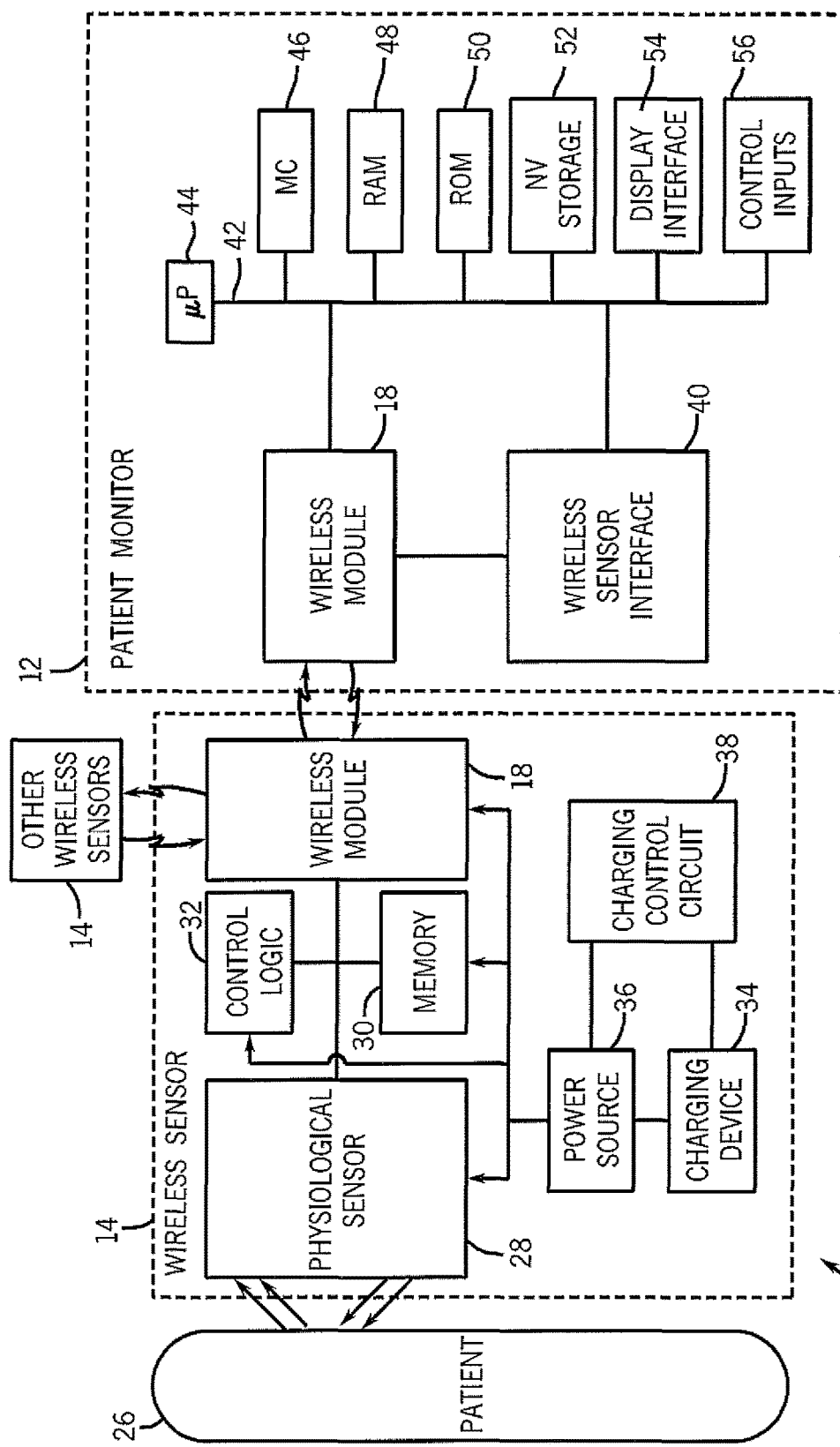
FIG. 2 is a block diagram of a wireless sensor and a patient monitor of the wireless web medical sensor system of FIG. 1, in accordance with an embodiment.

FIG. 2 is a block diagram of an embodiment of the medical sensor system 10 of FIG. 1. By way of example, embodiments of the system 10 may be implemented with any suitable medical sensors and patient monitor, such as those available from Nellcor Puritan Bennett LLC. The system 10 may include the patient monitor 12 and two or more medical sensors 14, and may obtain, for example, a photoplethysmographic signal, a patient body temperature, a respiration rate, a patient blood pressure, an electrocardiogram (ECG) signal, an electroencephalogram (EEG) signal, and/or pulse transit time, and so forth.

Each wireless medical sensor 14 may attach to a patient 26. Physiological sensor circuitry 28 in the wireless medical sensor 14 may obtain physiological information from the patient 26. By way of example, if the medical sensor 14 is a photoplethysmographic sensor, the physiological sensor circuitry 28 may include an emitter 22 and a detector 24. The emitter 22 may emit light of certain wavelengths into the patient 26. The detector may detect light that is transmitted or reflected through the patient 26. Regardless of the type of physiological information gathered by the physiological sensor circuity 28, the physiological sensor circuitry 28 may include amplification, low pass filter, and/or analog-to-digital conversion circuitry that may amplify and digitize raw physiological signals. The resulting digital physiological signals may be processed in the medical sensor 14 or in the patient monitor 12 to obtain physiological parameters related to the patient 26.

The digital signals output by the physiological sensor circuity 28 may be stored in memory 30 and/or queued in the wireless module 18 for transmission to a wireless module 18 of the patient monitor 12 or of other wireless medical sensors 14. Control logic 32 or a local microprocessor may control the operation of the wireless medical sensor 14 based at least in part on the meaning of the physiological information detected by the physiological sensor circuitry 28. In certain embodiments, the control logic 32 may control the operation of both the physiological sensor circuitry 28 and the wireless module 18. In certain other embodiments, the physiological sensor circuitry 28 and the wireless module 18 may operate independently of the control logic 32.

The control logic 32 may carry out certain algorithms regarding the operation of the medical sensor 14. Many such algorithms are discussed in greater detail below with reference to FIGS. 7-12. By way of example, the control logic 32 may assess one or more factors to determine whether the medical sensor 14 is to serve as a main communication point between the other wireless medical sensors 14 of the wireless web 16 and the patient monitor 12, as presently depicted in FIG. 2. Additionally or alternatively, the control logic 32 may assess one or more factors, including whether the signals from the physiological sensor circuitry 28 indicate a condition or disease, to determine a data update rate level. Based on the determined data update rate level, the control logic 32 may cause the wireless medical sensor 14 to operate in a more power-conservative manner when the patient 26 is healthy and/or stable, and/or to operate in a more active manner when the patient 26 is suffering from a condition or disease and/or is unstable.

In some embodiments, the control logic 32 and/or a local microprocessor may include processing capabilities for determining data of interest from the raw digital signals from the physiological sensor circuitry 28. Such data of interest may include, for example, $SpO_2$ readings, pulse rate, measurement of total hemoglobin, and so forth. The data of interest may require substantially less bandwidth for transmission to the patient monitor 12 than the raw digital signals from the physiological sensor circuitry 28. However, processing the raw digital signals to obtain such data of interest may consume a significant amount of power.

As mentioned above, the wireless medical sensors 14 may be low-power medical sensors that operate on batteries and/or use power obtained from various energy harvesting techniques, such as piezoelectric energy harvesting, inductive energy harvesting, and/or thermoelectric energy harvesting. One such energy harvesting charging device 34 may supply power to a power source 36. A charging control circuit 38 may allow for the adaptive control of wireless energy harvested from the charging device 34. In one embodiment, the power source 36 may include one or more batteries, such as a rechargeable battery that may be user-removable or may be secured within the housing of the sensor 14. Additionally or alternatively, the power source 36 may include one or more capacitors for storage of charge.

The charging control circuit 38 may, for example, include a processing circuit or control logic that may determine the current level of charge remaining in the power source 36, as well as the current amount of power being harvested by the charging device 34. By way of example, the charging control circuit 38 may determine if the charging device 34 is generating too little power to charge the power source 36. If so, the charging control circuit 38 may provide an indication to the control logic 32 or to the patient monitor 12, via the wireless module 18, that the power supply of the wireless medical sensor 14 is diminishing.

Each wireless sensor 14 may operate using relatively little power. To reduce the amount of power consumed, the wireless module 18 of each wireless medical sensor 14 may communicate using low-power wireless signals. As such, the wireless medical sensors 14 generally may communicate only with other local wireless medical sensors 14. According to the wireless protocol employed by the wireless module 18, the medical sensors 14 may form a wireless web 16. This wireless web 16 may propagate communication among the wireless medical sensors 14 to a main communication medical sensor 14 that communicates directly with the patient monitor 12. The main communication medical sensor 14 may transmit the physiological information gathered by all the medical sensors 14.

The digital physiological signals from the many wireless medical sensors 14 may be received by the wireless module 18 of the patient monitor 12, which generally may communicate only with the main communication wireless medical sensor 14. The wireless module 18 may transfer the received physiological signals to wireless sensor interface circuitry 40 and/or to a bus 42 connected to a general- or special-purpose microprocessor 44. In some embodiments, the microprocessor 44 may issue instructions, such as a particular data update rate level at which to operate, to the wireless medical sensors 14 via the wireless module 18.

In certain embodiments, the medical sensors 14 may not process the raw physiological signals into data of interest. As such, the wireless sensor interface circuitry 40 may perform initial processing on certain of the raw physiological signals before transferring the output to the bus 42. Among other things, the wireless sensor interface circuitry 40 may separate and identify the signals from the many medical sensors 14 before the signals are processed further by the microprocessor 44.

The microprocessor 44 on the bus 42 may govern various operations of the patient monitor 12. Such operations may include the determination of various physiological parameters based on data from the medical sensor 14, as well whether the medical sensors 14 should be operating at a higher or lower data update rate level based on a status of the patient 26. A network interface card (NIC) 46 may enable the patient monitor 12 to communicate with external devices on a network. Random access memory (RAM) 48 may provide temporary storage of variables and other data employed while carry out certain techniques described herein, while read only memory (ROM) 50 may store certain algorithms, such as those disclosed herein for ascertaining the data update rate level for the operation of the wireless medical sensors 14. Though nonvolatile storage 52 generally may store long-term data, the nonvolatile storage 52 also may store the algorithms described herein.

The patient monitor 12 may include other components, such as a display interface 54 and control inputs 56. The display interface 54 may enable the patient monitor 12 to indicate on the display 20 various physiological parameters obtained by the wireless medical sensors 14. Control inputs 56 may enable a physician or other medical practitioner to vary the operation of the patient monitor 12.

Figure 3:
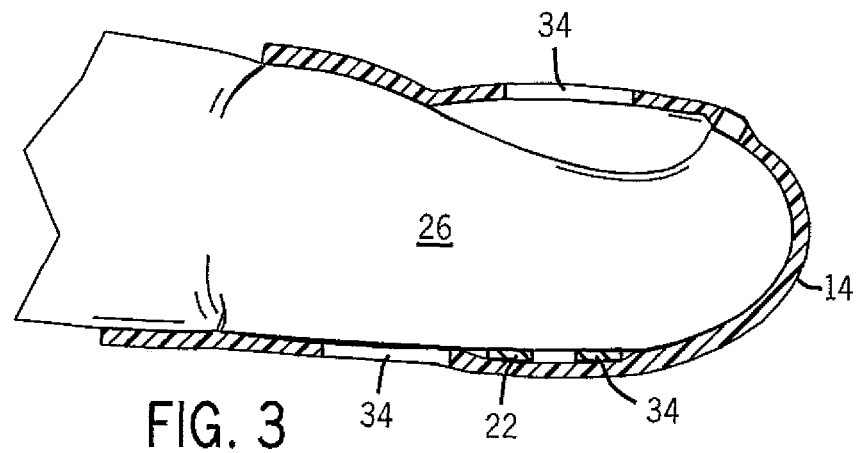
FIGS. 3-5 are schematic views of a wireless finger pulse oximetry sensor having energy harvesting capabilities for use with the system of FIG. 1, in accordance with an embodiment.
Figure 4:
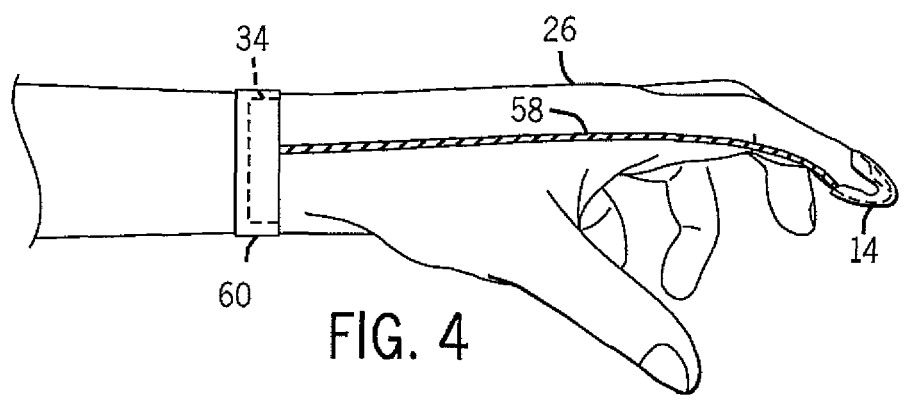
Figure 5:
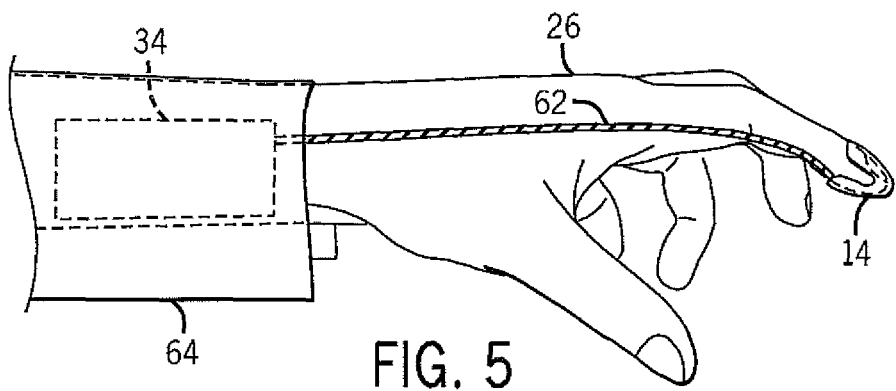
Figure 6:
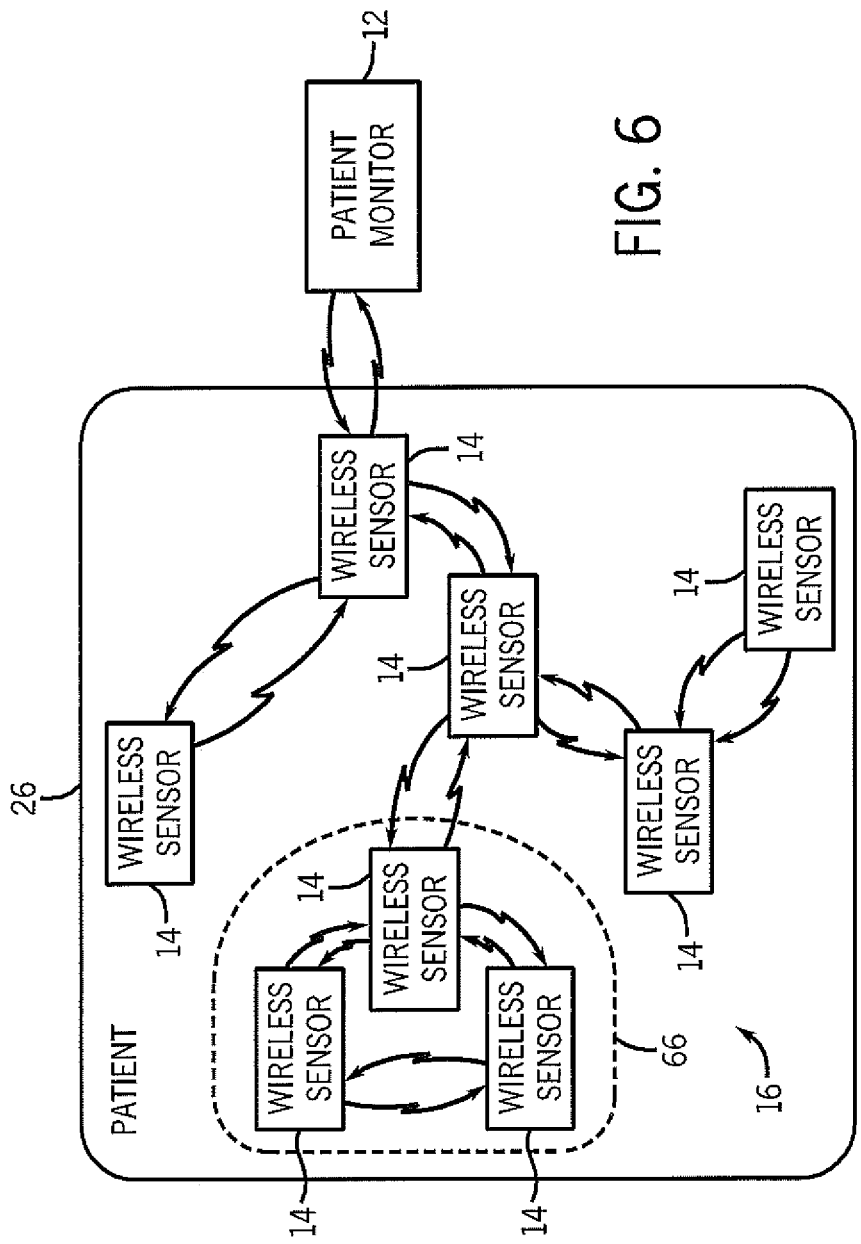
FIG. 6 is a block diagram of a self-assembling wireless web of medical sensors on a patient, in accordance with an embodiment.

As noted above, the wireless medical sensors 14 may utilize charging devices 34 to harvest energy. FIGS. 3-5 represent embodiments of wireless medical sensors 14 that employ varying configurations of charging devices 15. FIG. 3 illustrates various placement locations of one or more charging devices 34 in conjunction with a medical sensor 14. In the embodiment of FIG. 6, the medical sensor 14 may be utilized in conjunction with a finger of a patient 26. As may be seen, an emitter 22 and a detector 24 (representing externally visible components of the physiological sensor circuitry 28), as well as the wireless module 18 are illustrated as elements of the medical sensor 14. As depicted, the emitter 22 and detector 24 may be arranged in a reflectance-type configuration in which the emitter 22 and detector 24 are typically placed on the same side of the sensor site. Reflectance type sensors may operate by emitting light into the tissue (e.g., the finger of the patient 26) and detecting the reflected light that is transmitted and scattered by the tissue. That is, reflectance type sensors detect light photons that are scattered back to the detector 24. The medical sensor 14 may alternatively be configured as a transmittance type sensor whereby the emitter 22 and detector 24 are typically placed on differing sides of the sensor site. In this manner, the detector 24 may detect light that has passed through one side of a tissue site to an opposite side of the tissue site.

As illustrated in FIG. 3, the medical sensor 14 may also include one or more charging devices 34. The charging devices 34 may include, for example, piezoelectric energy harvesters, inductive energy harvesters, and/or thermoelectric energy harvesters. In one embodiment, a charging device 34 may be located on a top side of the sensor 14. Additionally and/or alternatively, a charging device 34 may be located on the bottom side of the medical sensor 14. Each of these charging devices 34 may be integrated into the medical sensor 14, or affixed thereto. Furthermore, these charging devices 34 may operate independently, or may be electrically coupled to one another to increase the overall energy that may be harvested for use by the medical sensor 14. Additionally, one or more charging stations 34 external to the medical sensor 14 may be utilized.

FIG. 4 illustrates an embodiment whereby the charging device 34 is located externally from the medical sensor 14. As illustrated, the charging device 34 may be attached to the medical sensor 14 via a lead 58. The lead 58 may be an electrical conductor, such as a power cable, that transmits harvested power to the medical sensor 14. The lead 58 may terminate with the charging device 34 which may be integrated into (or be attached to) a bracelet 60. The bracelet 60 may be, for example, a medical bracelet. Furthermore, the lead 58 may be connected to and separated from the charging device 34. That is, the lead 58 may be separable (i.e., releasable) from the charging device 34, the bracelet 60, and/or the medical sensor 14. Alternatively, the lead 58 may be permanently affixed to the charging device 34 and/or the bracelet 60. Regardless, by separating the charging device 34 from the medical sensor 14, more available area in the bracelet 60 may be available for harvesting of energy. That is, with greater area available for the charging device 34, a greater number of energy harvesters in the charging device 34 may be utilized, thus increasing the overall amount of energy that may be harvested.

FIG. 5 illustrates a second embodiment whereby the charging device 34 may be located externally from the medical sensor 14. As illustrated, the charging device 34 may be attached to the medical sensor 14 via a lead 62. The lead 62 may be an electrical conductor, such as a power cable, that transmits power to the medical sensor 14 and may terminate with the charging device 34 which may be integrated into (or be attached to) a garment 64. Again, the lead 62 may be separable (i.e., releasable) from the charging device 34, the garment 64, and/or the medical sensor 14. The garment 64 may be, for example, a shirt or a sleeve of a shirt. The use of the a garment 64 to house the charging device 34 may allow for the charging device 34 to be expanded in size, or for more than one charging devices 34 to be utilized in conjunction, while still allowing for the garment 64 to be comfortably worn. Thus a greater number of energy harvesters may be utilized, which may increase the overall amount of energy that may be harvested. Additionally, by utilizing a large area, such as the garment 64, movements of the patient 26 across a plurality of regions of the patient 26 may be utilized to harvest energy. That is, movements in the chest, arms, etc. of the patient 26 may be translated into power for use by the medical sensor 14. In this manner, a greater number of movements of the patient 26 may be harvested into power for use with the medical sensor 14.

Such low-power wireless medical sensors 14 may self-assemble into a wireless web 16 on a patient 26, as shown in FIG. 6. Each wireless medical sensor 14 of the wireless web 16 may convey information from one local sensor 14 to another local sensor 14, propagating information to and from the patient monitor 12 using such a wireless protocol as may relate to the IEEE 802.15.4 standard, which may include, for example, ZigBee, WirelessHART, and/or MiWi. Additionally or alternatively, the medical sensors 14 may be capable of communicating using the Bluetooth standard or one or more of the IEEE 802.11.x standards. In some embodiments, the wireless communication may involve optical communication, such as free space optics (FSO), using light emitting diodes (LEDs) and/or laser diodes (LDs). Generally, only one of the medical sensors 14 of the wireless web 16 may communicate with the patient monitor 12 at any given time. Moreover, the medical sensors 14 may generally only communicate using low-power signals to other nearby medical sensors 14. In this way, the medical sensors 14 of the wireless web 16 may conserve power.

As discussed below, the wireless web 16 of medical sensors 14 may self-assemble by determining which medical sensor 14 may communicate with the patient monitor 12. The control logic 32 of each wireless medical sensor 14 may consider one or more factors to decide whether that medical sensor 14 should be the main communication point for the wireless web. Moreover, as conditions change (e.g., as the patient 26 rotates with respect to the patient monitor 12 or as power supplies vary in certain sensors 14), the sensors 14 wireless web 16 may select a new medical sensor 14 to serve as the main point of communication with the patient monitor 12. Embodiments of methods for determining which medical sensor 14 should serve as the main point of communication are described below with reference to FIGS. 7-10.

In the same manner, certain wireless sensors 14 may form a node 66. The medical sensors 14 of the node 66 may select one of the medical sensors 14 of the node 66 to serve as a main communication point with the rest of the wireless web 16. Forming a node 66 of medical sensors 14 may be useful, for example, if the sensors 14 of the node 66 generally operate at a higher or lower data update rate level or a different synchronization from than the rest of the medical sensors 14 of the wireless web 16. Under such conditions, most of the sensors 14 of the node 66 may operate at a single synchronization or data update rate level, and only one sensor 14 may operate with both the sensors 14 of the node 66 and the rest of the wireless web 16, thereby conserving power among most of the medical sensors 14 of the node 66.

As discussed below, the wireless medical sensors 14 may conserve power by operating at a data update rate level dependent on a status of the patient 26. Although the data rate employed by a medical sensor 14 may remain constant (e.g., 100 kbps) or may vary based on the wireless protocol and/or signal to noise ratio (SNR), the data update rate level (e.g., update once every second, once every 30 seconds, or once every minute, and so forth) may change based on the status of the patient 26. For example, the data update rate level may be lower when the patient 26 is stable and/or healthy, and the data update rate level may be higher when the patient 26 is unstable and/or has a condition or disease. When the data update rate level is relatively low, the wireless medical sensors 14 of the wireless web 16 may deactivate for periods of time. The medical sensors 14 may awake at coordinated and/or synchronized times to take physiological measurements and communicate such measurements through the wireless web 16 to the patient monitor 12. It should be noted, however, that the times during which the medical sensors 14 are awake may be coordinated such that not all of the medical sensors 14 are awake at the same time, which could create data traffic problems as all of the medical sensors 14 may attempt to transmit at the same time. When the data update rate level is relatively high, the wireless medical sensors 14 may deactivate for relatively shorter periods of time, or may not deactivate at all. Embodiments of methods for determining such a data update rate level is described below with reference to FIGS. 11 and 12.

Figure 7:
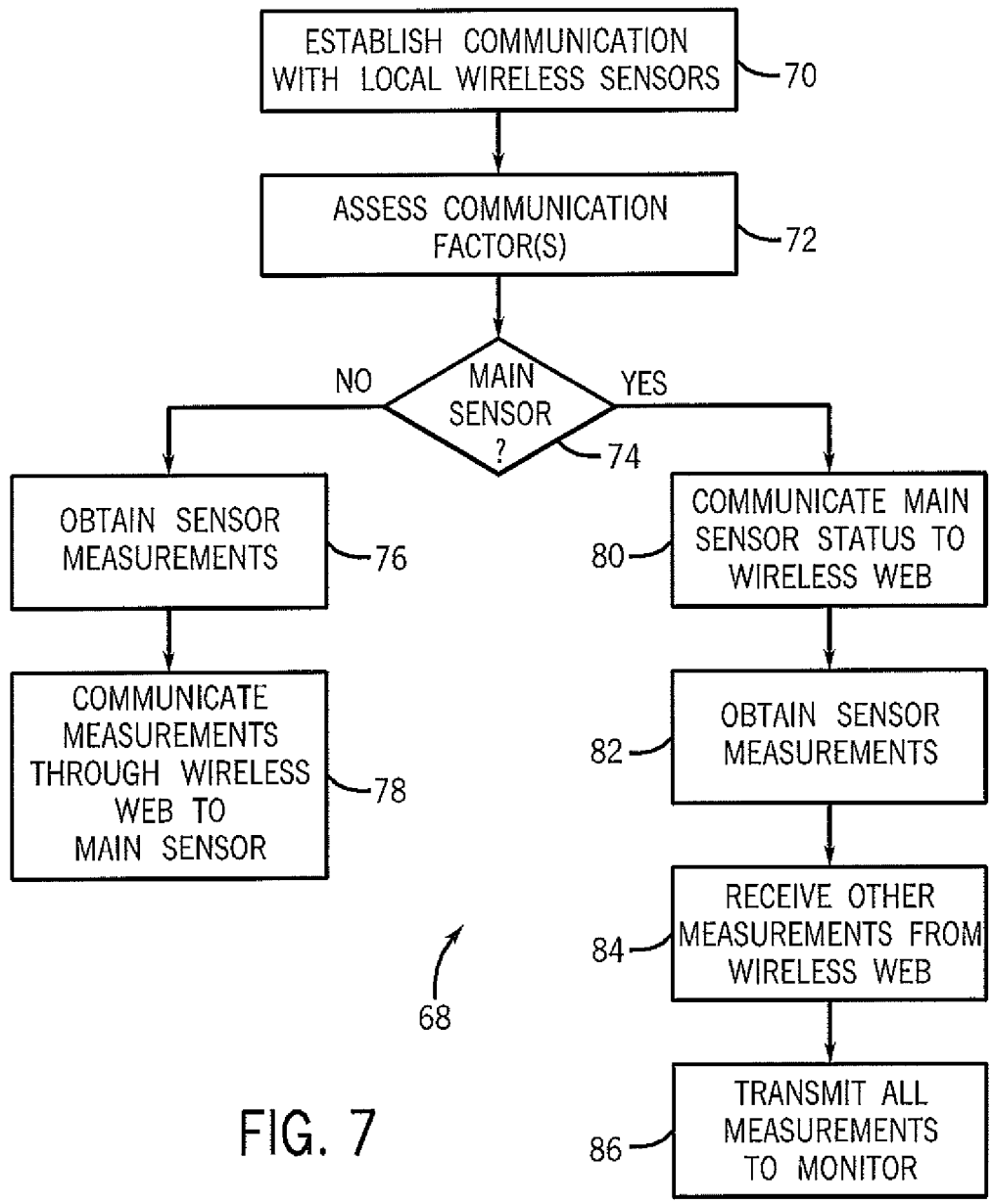
FIG. 7 is a flowchart representing an embodiment of a method for initializing the wireless web of wireless medical sensors of FIG. 6.

FIG. 7 depicts a flowchart 68, which describes an embodiment of a method for initializing the wireless web 16 of medical sensors 14. In a first step 70, several wireless medical sensors 14 that have been placed on a patient 26 may discover one another and establish wireless communication to each other and/or with the patient monitor 12 via wireless modules 18. The wireless medical sensors 14 may synchronize their operating times such that communication may take place for all the sensors 14 at approximately but not necessarily the same time, to avoid collisions in data transmission. In this way, the medical sensors 14 may conserve power spent on wireless communication.

In step 72, each medical sensor 14 or a subset of the medical sensors 14 of the newly formed wireless web 16 may assess one or more communication factors. As described below with reference to FIG. 8, these communication factors may include, for example, the proximity of the sensor 14 to the patient monitor 12, the selection of a button or switch on the medical sensor 14, a charge level of the power source 36, an instruction from the patient monitor 12, and/or a signal quality of communication to and from the sensor 14. In decision block 74, each medical sensor 14 or the subset of the medical sensors 14 may weigh the assessed factors to ascertain whether it should serve as the main communication medical sensor 14. In some embodiments, the medical sensors 14 may also provide an indication of the assessed factors to the rest of the wireless web 16. The assessments by other medical sensors 14 of the wireless web 16 may also affect the determination made by each medical sensor 14 or the subset of medical sensors 14.

If the assessed factors indicate to a medical sensor 14 that it should not serve as the main communication medical sensor 14, the medical sensor 14 may begin operating at a default data update rate level as an ordinary member of the wireless web 16. As such, in step 76, the medical sensor 14 may begin to take periodic physiological measurements. In step 78, the medical sensor 14 may communicate those measurements through the wireless web 16 to the main communication sensor 14. As such, the medical sensor 14 may also forward messages received from other medical sensors 14 of the wireless web 16. However, it should be noted that if a medical sensor 14 is used to forward messages from other medical sensors 14, it may be listening and thus awake at all times, at the cost of power consumption.

If the assessed factors indicate to a medical sensor 14 that it should serve as the main communication medical sensor 14, the medical sensor 14 may, in step 80, communicate as such to the other sensors 14 of the wireless web 16. In step 82, the medical sensor 14 may begin operating at a default data update rate level as the main communication medical sensor 14 of the wireless web 16. As such, the medical sensor 14 may begin to take periodic physiological measurements. In step 84, the medical sensor 14 may receive physiological measurements from other medical sensors 14. In step 86, the medical sensor 14 may communicate all of the measurements to the patient monitor 12.

Figure 8:
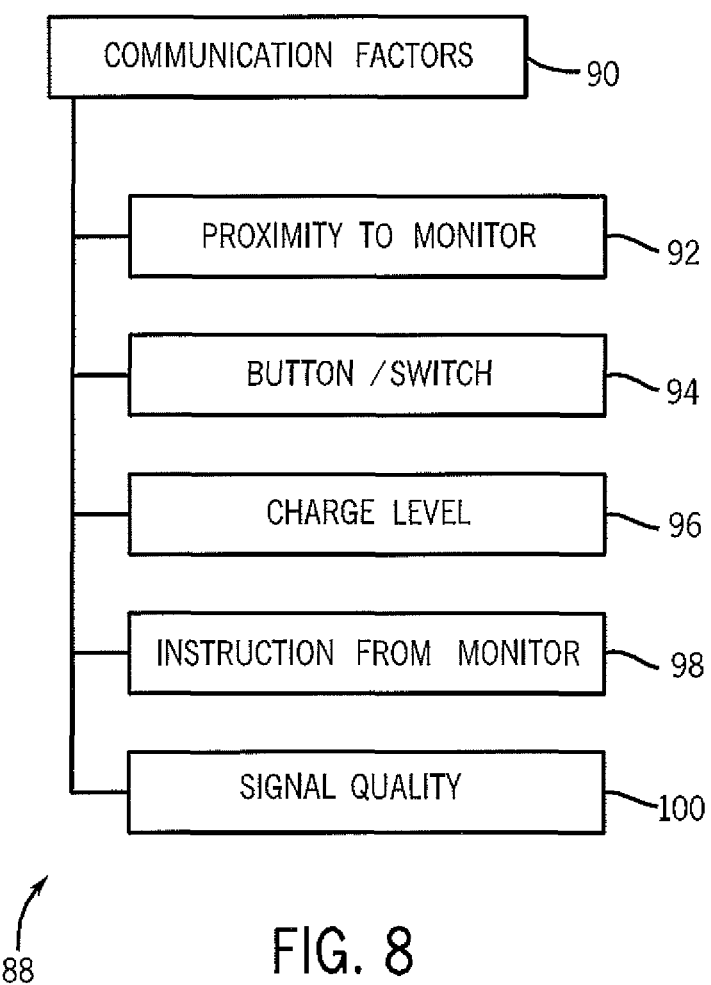
FIG. 8 is a schematic diagram representing certain factors for consideration during the initialization of the wireless web of medical sensors, in accordance with an embodiment.

FIG. 8 represents a factor diagram 88 listing communication factors 90 that may be considered by the medical sensors 14 in step 72 of the flowchart 68 of FIG. 7. The communication factors 90 listed in FIG. 8 are intended to be exemplary and not exclusive, and the particular communication factors 90 considered by the medical sensor 14 may be predetermined or may be selected based on a current status of a patient 26.

A first factor 92 of the communication factors 90 may relate to the proximity of the medical sensor 14 to the patient monitor 12. The medical sensor 14 may assess the proximity of the patient monitor 12 based on the received signal strength of a wireless signal from the wireless module 18 of the patient monitor 12. Additionally or alternatively, the medical sensor 14 may be programmed with an indication of its intended body location placement, and may estimate its proximity to the patient monitor 12 based on, for example, how close to the medical sensor 14 should be to the outer regions of the patient.

A second factor 94 of the communication factors 90 may include whether a button or switch on a medical sensor 14 has been activated by a clinician. A clinician may do so, for example, to indicate that the medical sensor 14 is located nearby to the patient monitor 12.

A third factor 96 of the communication factors 90 may be the current charge level of the power source 36. The current charge level may be ascertained by the control logic 32 by way of a message from the charging control circuitry 38. A higher charge level may indicate that the medical sensor 14 may be able to tolerate the increased power consumption that may occur with longer-range wireless communication with the patient monitor 12.

A fourth factor 98 of the communication factors 90 may be an instruction from the patient monitor 12. In some embodiments, the patient monitor 12 may determine which of the medical sensors 14 of the wireless web 16 should be the main point of communication, based on the one or more of the communication factors 90 or other considerations. By way of example, the patient monitor 12 may instruct the wireless web 16 to rotate which medical sensor 14 serves as the main communication sensor 14, which may result in a more evenly distributed consumption of power among the medical sensors 14.

A fifth factor 100 of the communication factors 90 may be the signal quality of wireless communication to and from a particular wireless medical sensor 14. For example, if the medical sensor 14 closest to the patient monitor 12 has difficulties establishing connections between other medical sensors 14 of the wireless web 16, a different medical sensor 14 should most likely serve as the main communication sensor 14.

Figure 9:
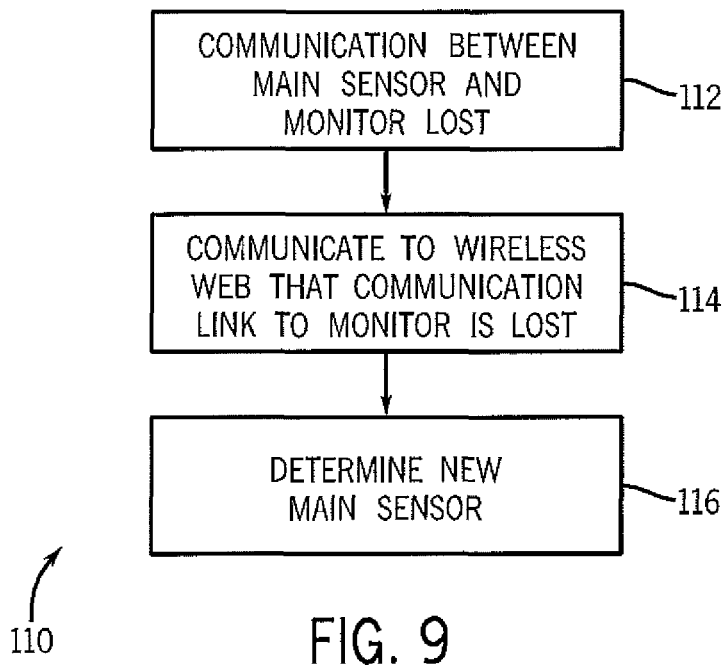
FIGS. 9 and 10 are flowcharts representing embodiments of methods for re-initializing the wireless web of medical sensors when communication between a main sensor and/or the patient monitor is lost.

Occasionally, after the wireless web 16 has been established and the medical sensors 14 are operating in a normal fashion, the main communication sensor 14 may lose communication with the patient monitor 12 or the rest of the wireless web 16. Turning to FIG. 9, a flowchart 110 represents an embodiment of a method for reestablishing communication when, as shown in step 112, the main communication sensor 14 has lost communication with the patient monitor 12. In step 114, the main communication sensor 14 may indicate as such to the other medical sensors 14 of the wireless web 16. In step 116, the medical sensors 14 of the wireless web 16 may determine a new main communication sensor 14 in an effort to reestablish communication with the patient monitor 12. Step 116 may take place in substantially the same manner as step 72 and decision block 74 of the flowchart 68 of FIG. 7.

Figure 10:
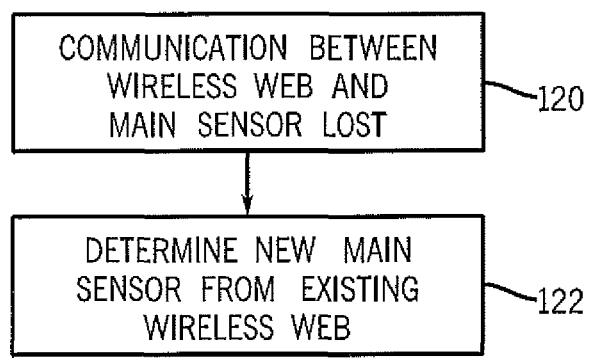

FIG. 10 illustrates a flowchart 118 of an embodiment of a method for reestablishing communication when, as shown in step 120, the main communication sensor 14 has lost communication with the other medical sensors 14 of the wireless web 16. In step 122, the other medical sensors 14 of the wireless web 16 may ascertain that such communication has been lost, and may determine a new main communication sensor 14 in an effort to reestablish communication with the patient monitor 12. Step 122 may take place in substantially the same manner as step 72 and decision block 74 of the flowchart 68 of FIG. 7.

Figure 11:
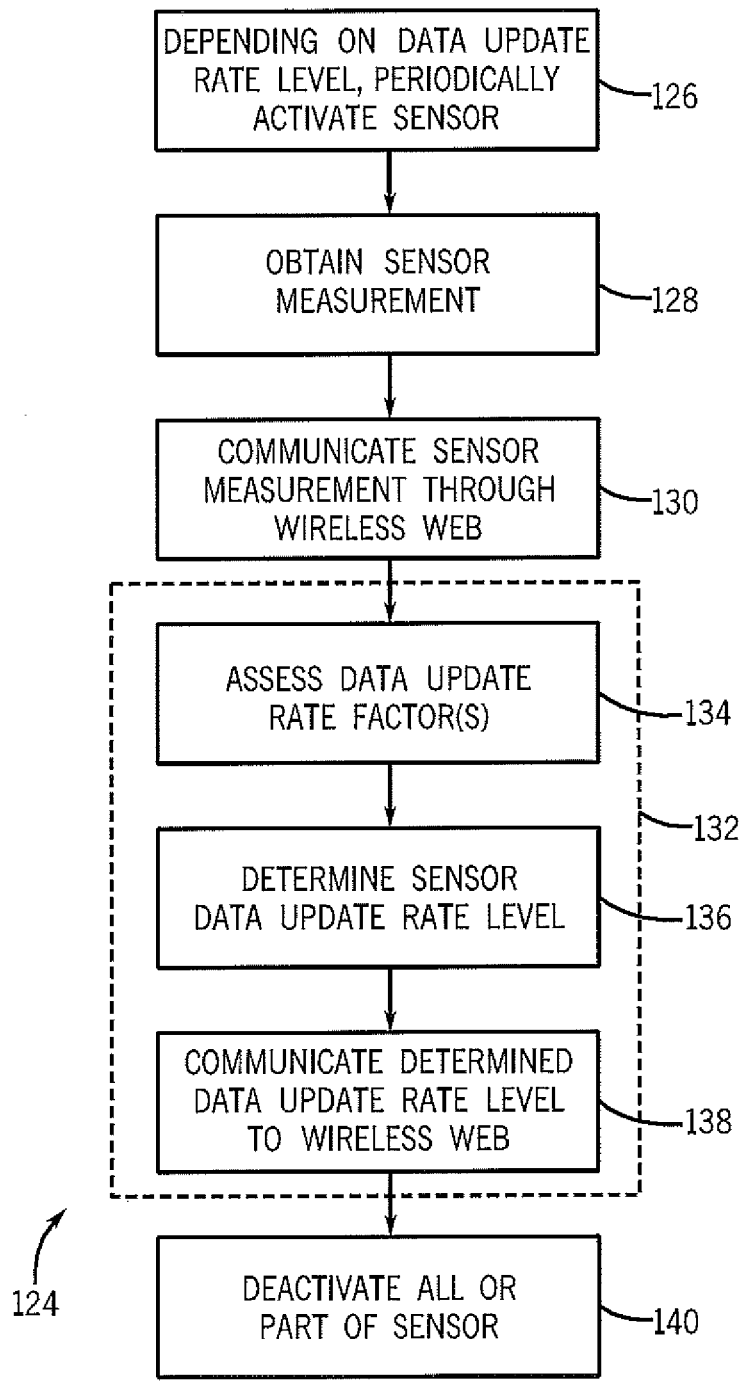
FIG. 11 is a flowchart representing an embodiment of a method for operating the wireless web of medical sensors.

FIG. 11 is a flowchart 124 of an embodiment of a method for operating the medical sensors 14 of the wireless web 16 to conserve power. Instructions for performing the method of the flowchart 124 may be stored in the memory 30 and/or carried out by the control logic 32 of each medical sensor 14. In general, the flowchart 124 may begin after a period in which the medical sensor 14 has been periodically deactivated to save power.

In a first step 126, each medical sensor 14 may individually awaken periodically. The period may depend upon, for example, the current data update rate level employed by the medical sensors 14. As noted above and described in greater detail below, the data update rate level may be based on a current status of a patient 26. Because communication among the many wireless medical sensors 14 generally may be synchronized, all of the medical sensors 14 of the wireless web 16 may awaken at the same time. In step 128, the medical sensors 14 may obtain a physiological measurement of the patient 26 and, in step 130, the medical sensors 14 may communicate their measurements through the wireless web 16 to the patient monitor 12. Step 130 may also include other inter-sensor wireless communication, which may ensure that the wireless modules 18 of the sensors 14 remain synchronized and/or which may propagate instructions from the patient monitor 12.

The wireless medical sensors 14 may occasionally enter a process 132 to evaluate the data update rate level at which to operate. Generally, the process 132 may not occur every time that the medical sensors 14 awaken and carry out wireless communication. Instead, the process 132 may take place periodically or when the measured physiological parameters of step 128 indicate that the patient 26 is becoming less stable. Additionally or alternatively, the process 132 may occur not on the individual wireless medical sensors 14, but rather on the patient monitor 12.

In the first step of the process 132, step 134, one or more data update rate level factors may be considered. Exemplary data update rate level factors are described in greater detail below with reference to FIG. 12. In step 136, based on the assessment of step 134, the medical sensors 14 may determine an appropriate data update rate level at which to operate. In step 138, the medical sensors 14 may communicate among one another their determinations. In certain embodiments, based on the communication of step 138, all of the medical sensors 14 may select the highest data update rate level determined by any of the other medical sensors 14. In other embodiments, the medical sensors 14 may operate at different data update rate levels, but each medical sensor 14 may store in their respective memories 30 the data update rate levels at which other local medical sensors 14 may operate.

Regardless of whether the process 132 takes place, in step 140, the medical sensors 14 may deactivate for a period of time that depends on the data update rate level. For example, if the data update rate level is relative low, the period of time may be relatively long. If the data update rate level is relatively high, the period of time may be relatively short. By way of example, the period of inactivity may be 1 second, 2 seconds, 5 seconds, 10 seconds, 30 seconds, 1 minute, 2 minutes, 5 minutes, 10 minutes, 30 minutes, 1 hour, 2 hours, 5 hours, etc. In certain embodiments, when the data update rate level is sufficiently high, the wireless medical sensors 14 may not deactivate. Following the period of deactivation, the medical sensors 14 may reawaken and repeat the flowchart 124.

Figure 12:
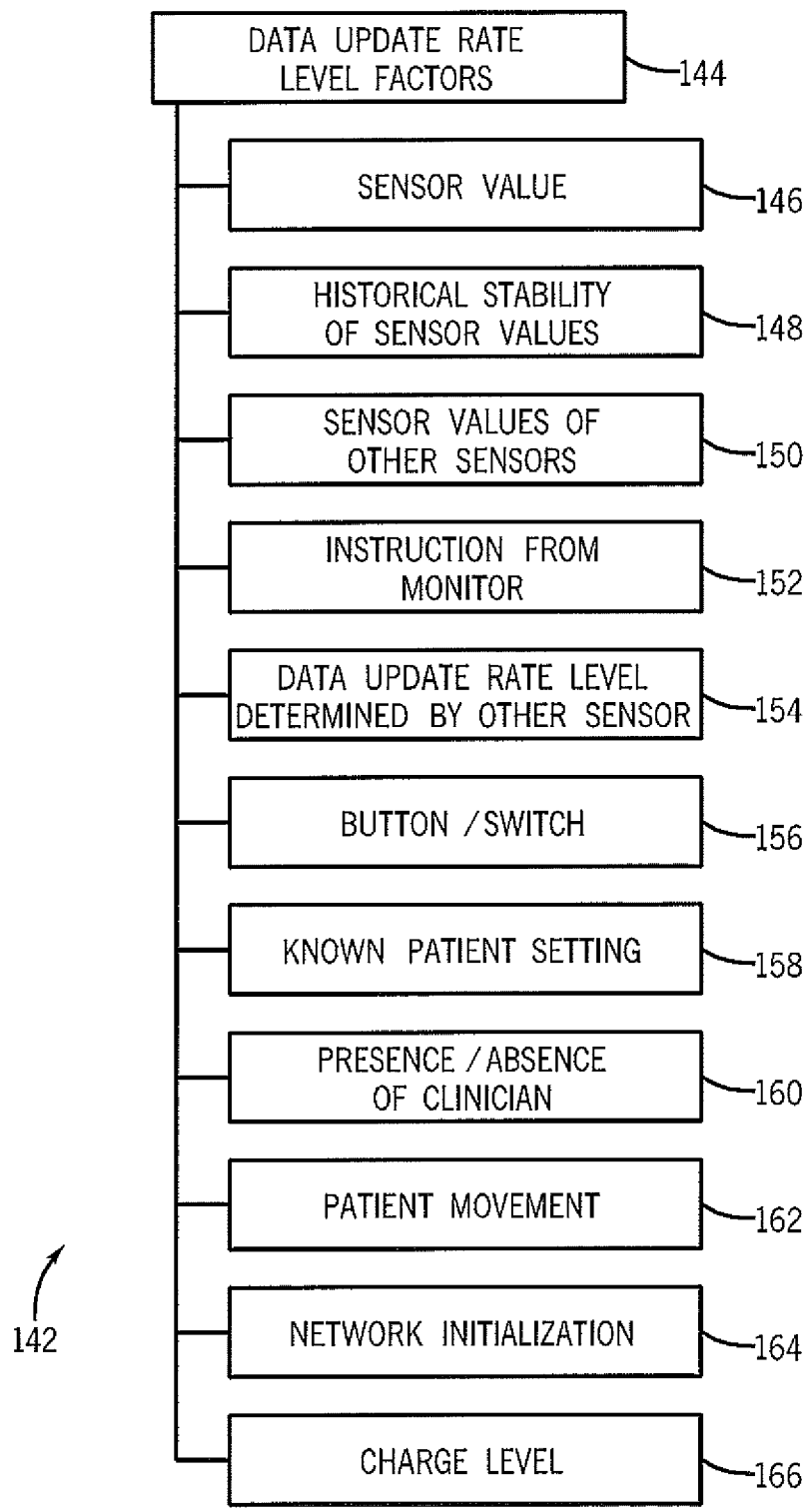
FIG. 12 is a schematic diagram representing certain factors for consideration for selecting a data update rate level used during the operation of the wireless web of medical sensors, in accordance with an embodiment.

As described above, in the first step 134 of the process 132, the wireless medical sensors 14 or the patient monitor 12 may assess one or more factors to determine the data update rate level. FIG. 12 represents a factor diagram 142 listing such data update rate level factors 144. The data update rate level factors 144 listed in FIG. 12 are intended to be exemplary and not exclusive, and the particular data update rate level factors 144 considered by the medical sensors 14 or patient monitor 12 may be predetermined or may be selected based on a current status of the patient 26. The considered factors may be weighted and/or scored, and the data update rate level may reflect a total weighted and/or scored value of the considered factors.

A first factor 146 of the data update rate level factors 144 may be a current value of a physiological measurement obtained in step 128. By way of example, the control logic 32 may be capable of sampling all or a portion of the digital signal provided by the physiological sensor circuitry 28. If so, the control logic 32 may occasionally sample the physiological measurement, storing the sampled measurement into the memory 30. If the sampled measurement is within a predetermined acceptable range of values, the factor 146 may weigh in favor of a comparatively lower data update rate level. If the sampled measurement is higher or lower than the predetermined acceptable range of values, the factor 146 may weigh in favor of a comparatively higher data update rate level.

By way of example, if the sampled measurement includes a respiration rate, a predetermined acceptable range of values for an adult patient may be a range of 12 to 20 breaths per minute. A respiration rate less than 12 breaths per minute or greater than 20 breaths per minute may weigh in favor of a higher data update rate level. In determining the data update rate level based at least in part on the factor 146, the control logic 32 may further consider how much the value of the sampled measurement varies beyond the predetermined acceptable range. In other words, the more the sampled value varies from the predetermined acceptable range, the more the factor 146 may weigh in favor of a higher data update rate level.

A second factor 148 of the data update rate level factors 144 may be the historical stability of recently sampled physiological measurements. If the sampled measurement is within a predetermined variability threshold over a recent historical period (e.g., 5 minutes), the factor 148 may weigh in favor of a relatively lower data update rate level. If the sampled measurement varies beyond the predetermined variability threshold, the factor 148 may weigh in favor of a relatively higher data update rate level. In determining the data update rate level based at least in part on the factor 148, the microprocessor 38 may further consider how much the sampled measurement has varied. For example, the greater the variability of the sampled measurement, the more the factor 148 may weigh in favor of a higher data update rate level.

A third factor 150 of the data update rate level factors 144 may be physiological measurements obtained by other medical sensors 14 of the wireless web 16. Such physiological measurements may be sampled and transmitted from one or more medical sensors 14 to other medical sensors 14 of the wireless web 16 for purposes of performing the assessment of step 134. Additionally or alternatively, each medical sensor 14 may sample measurements from other sensors as the measurements are propagated through the wireless web 16 toward the patient monitor 12.

Like the factors 146 and/or 148, if sampled physiological measurements from the other medical sensors 14 exceed a predetermined acceptable range of variability over a recent historical period, or if an absolute value exceeds a predetermined acceptable range of values, the factor 150 may weigh in favor of a higher data update rate level. Similarly, if the measurements from other sensors 14 remain within the predetermined acceptable range of variability over the recent historical period, or if the absolute value does not exceed the predetermined acceptable range of values, the factor 150 may weigh in favor of a lower data update rate level.

By way of example, if one of the medical sensors 14 is a temperature sensor, and a current patient temperature falls outside a predetermined acceptable range of values (e.g., a range of between 97.6° F. and 99.6° F.), the other medical sensors 14 may interpret the factor 150 as weighing in favor of a higher data update rate level. Also like the factors 88 and/or 90, in determining the data update rate level based at least in part on the factor 150, the medical sensors 14 may also consider how much the other sensor measurements have varied over time or how much the absolute value of the other sensor measurements vary beyond the predetermined acceptable ranges.

Express instructions received by the wireless web 16 of medical sensors 14 from the patient monitor 12 may constitute a fourth factor 152 of the data update rate level factors 144. As discussed above, the patient monitor 12 may occasionally transmit instructions the wireless medical sensors 14 of the wireless web 16. These instructions may indicate a particular data update rate level at which to operate, as determined by the patient monitor 12 or by a clinician. To provide one example, by pressing a button on the patient monitor 12, medical personnel may cause the patient monitor 12 to instruct the wireless medical sensor 14 to operate continuously without deactivating, which may represent the highest data update rate level observed by the wireless web 16 of medical sensors 14.

A fifth factor 154 of the data update rate level factors 144 may be the data update rate level determined by other medical sensors 14. By way of example, if one medical sensor 14 determines a relatively higher data update rate level, other medical sensors 14 may weigh the factor 154 in favor of a higher data update rate level. However, in some embodiments, if one medical sensor 14 determines a relatively lower data update rate level, other medical sensors 14 may not weigh the factor 154 in favor of either a higher or lower data update rate level.

A sixth factor 156 of the data update rate level factors 144 may be a press of a button or switch on the wireless medical sensor 14. If the button or switch is a single button and the button is pressed, the factor 156 may weigh in favor of a higher data update rate level. Similarly, if the button or switch is a switch with two or more settings (e.g., low, medium, high, etc.), the setting to which the button or switch has been moved may correspondingly weigh in favor of higher or lower data update rate levels, as appropriate. For example, because pressing the button or switch may cause the factor 156 to weigh in favor of a higher data update rate level, pressing the button or switch may result in the continuous operation of the medical sensors 14 of the wireless web 16.

A seventh factor 158 of the data update rate level factors 144 may be the current location of the patient 26, which may be indicated to the wireless medical sensors 14 via the patient monitor 12. Because the amount of data from the wireless medical sensors 14 that should be supplied to the patient monitor 12 may vary depending on whether the patient 26 is in surgery, in recovery, or undergoing other tests, the current location of the patient 26 may be considered as one of the data update rate level factors 144. Thus, if the patient 26 is currently located in a medical facility room where the patient 26 should be kept under especially close scrutiny, such as an operating room, the factor 158 may weigh in favor of a correspondingly higher data update rate level. If the patient 26 is currently located in a medical facility room where the patient 26 may be kept under less scrutiny, such as a recovery room, the factor 158 may weigh in favor of a lower data update rate level.

In determining the data update rate level based at least in part on the factor 158, the medical sensors 14 may give different locations different weights in favor of a higher or lower data update rate level. For example, if the current location is a testing room, such as a CT room, the factor 158 may weigh in favor of a comparatively higher data update rate level. However, the factor 158 may weigh even more heavily in favor of a higher data update rate level if the current location of the patient 26 is the operating room. Similarly, the sensors 14 may be instructed to stop transmitting data or use a very low data update rate level if the patient 26 is located in close proximity to an instrument which is sensitive to wireless interference. In such a case, if the sensors 14 include frequency hopping capabilities, the sensor 14 may select an alternate frequency or channel that does not interfere with nearby equipment or other sensors 14 located on other patients 26. In this way, data from a critically ill patient 26 or patient 26 in an operating room may be prioritized higher than patients 26 who are relatively stable.

An eighth factor 160 of the data update rate level factors 144 may be the presence or the absence of a clinician proximate to the patient 26, which may be supplied to the wireless medical sensors 14 via the patient monitor 12. For example, if a clinician enters a room where the patient 26 is currently located, the factor 160 may weigh in favor of a comparatively higher data update rate level. If the clinician exits the room, the factor 160 may weigh in favor of a comparatively lower data update rate level. In determining the data update rate level based at least in part on the factor 160, the medical sensors 14 may weigh the factor 160 more heavily in favor of a higher or lower data update rate level based on the number or patient assignment of clinicians present. For example, if a clinician that is not assigned to the patient 26 enters a room where the patient 26 is currently located, the factor 160 may not weigh as heavily in favor of a higher data update rate level as when a clinician that is assigned to the patient 26 enters the room.

A ninth factor 162 of the data update rate level factors 144 may be the movement of the patient 26, which may be indicated to the wireless medical sensors 14 via the patient monitor 12. Additionally or alternatively, if one of the medical sensors 14 includes a movement sensor, such as an accelerometer, an indication of patient 26 movement may be propagated through the wireless web 16. If the patient 26 is currently moving, indicating that the patient 26 is not at rest or is being moved from one room to another, the factor 162 may weigh in favor of a comparatively higher data update rate level. If the patient 26 is not currently moving, the factor 162 may weigh in favor of a comparatively lower data update rate level. Additionally, the amount of current patient movement may further affect the weight of the factor 162 in favor of a comparatively higher or lower data update rate level. In another example, transmission of the heart rate of the patient 26 may be suppressed if an accelerometer detects excessive motion artifact, and the calculated heart rate may be less likely to be accurate than a previous value.

A tenth factor 164 of the data update rate level factors 144 may be an initialization status of the wireless medical sensors 14. For a predetermined period of time while the wireless web 16 of sensors 14 is being initialized (e.g., 5 minutes), the data update rate level of the sensors 14 may be temporarily increased dramatically, such that the medical sensors 14 do not deactivate to save power. By supplying a raw data stream during the initialization of the wireless web 16, a clinician or other medical personnel may properly fit the medical sensors 14 to the patient 26.

An eleventh factor 166 of the data update rate level factors 144 may be an amount of power remaining in the power sources 36 of the wireless medical sensors 14. If the power sources 36 of the sensors 14 have more than a certain amount of remaining power, the factor 166 may weigh in favor of a comparatively higher data update rate level. If the power sources 36 have less than the predetermined amount of remaining power, the factor 166 may weigh in favor of a comparatively lower data update rate level. This factor 166 may also account for the transmit power required to send error-free data at the last update. For instance, when the patient 26 is relatively far from the receiver of the patient monitor 12, more transmit power may be required, so less frequent updates may take place, especially at lower power source 36 reserves.

Figure 13:
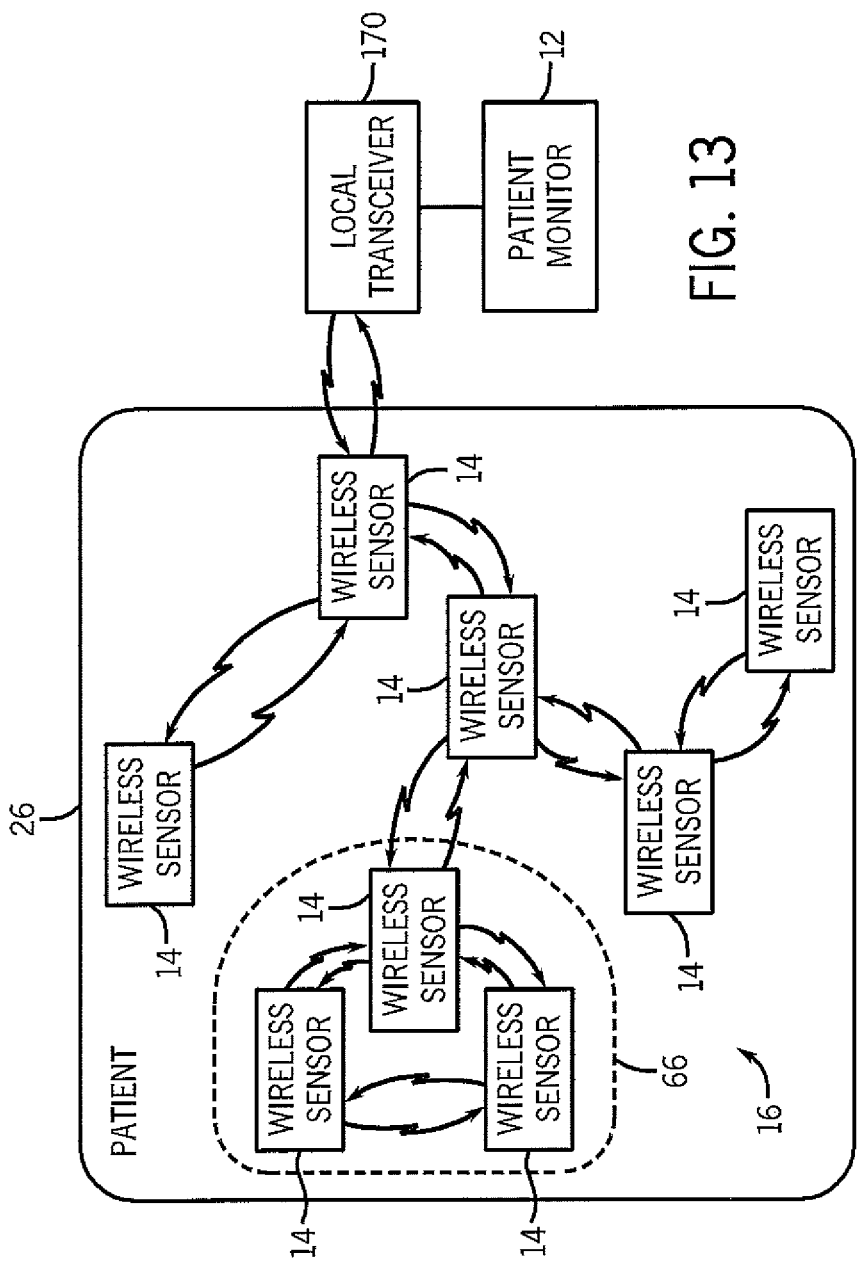
FIG. 13 is a block diagram of a self-assembling wireless web of medical sensors that communicates with a patient monitor via a local (e.g., bedside) transceiver, in accordance with an embodiment.

FIGS. 13-16 represent alternative embodiments of the configuration of the wireless web 16 of medical sensors 14. FIG. 13 illustrates an embodiment in which a local transceiver 170 receives communication from a main communication sensor 14 of the wireless web 16 of medical sensors 14. In the embodiment of FIG. 13, a number of the wireless medical sensors 14 may form a wireless web 16 while attached to a patient 26. In some embodiments, certain sensors 14 may form a separate node 66.

The main communication medical sensor 14, which generally may be the sole medical sensor 14 that communicates wirelessly with devices outside of the wireless web 16, may not communicate directly with a wireless module 18 integrated into the patient monitor 12, but may rather communicate wirelessly with the local transceiver 170. The local transceiver 170 may facilitate communication between the main communication medical sensor 14 and the patient monitor 12 using a wired or wireless connection to the patient monitor 12. Because the local transceiver 170 may be placed nearby to a patient 26 and/or placed in or integrated into a medical bed in which the patient 26 rests, the main communication medical sensor 14 may consume a reduced amount of power due to a reduced transmission distance for wireless communication.

Figure 14:
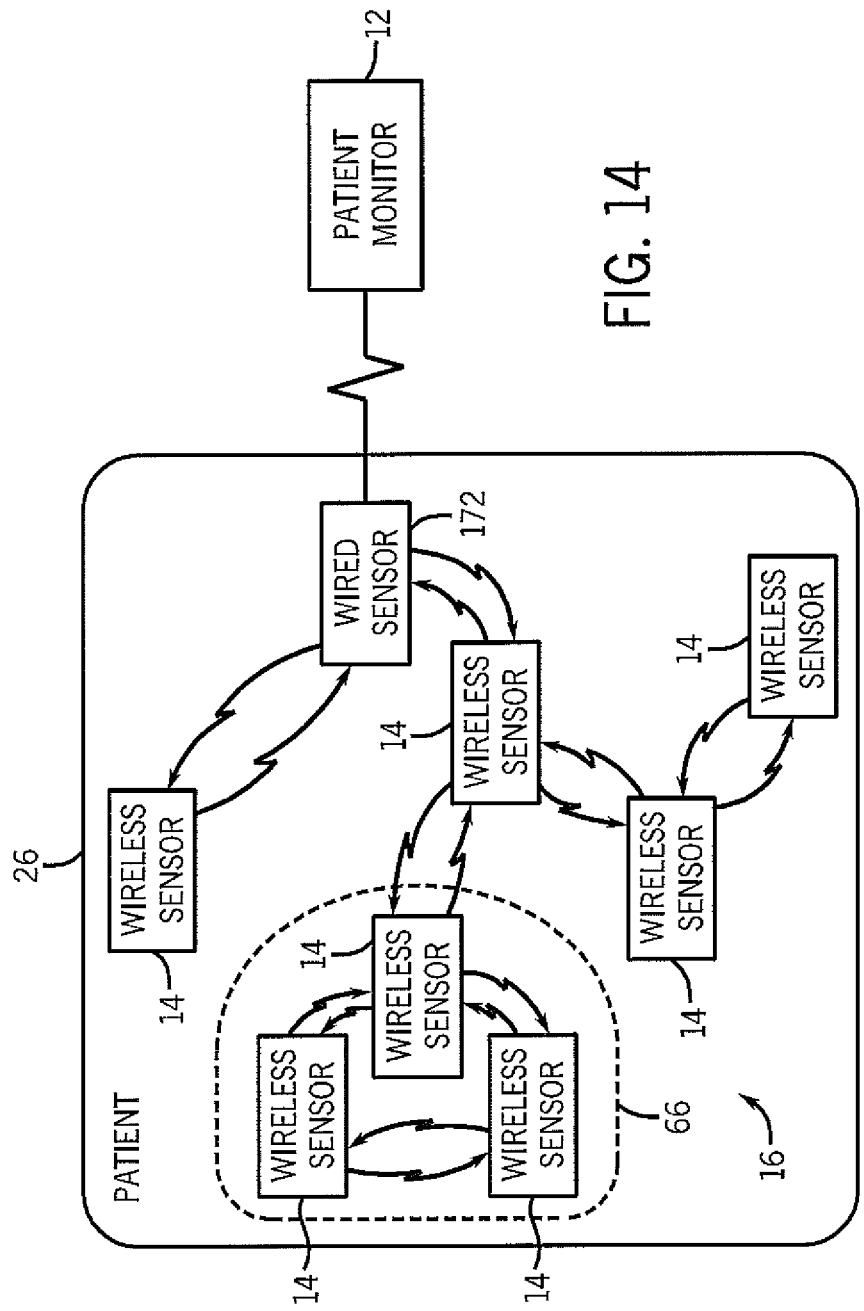
FIG. 14 is a block diagram of a self-assembling wireless web of medical sensors that communicates with a patient monitor via a wired medical sensor with wireless capabilities, in accordance with an embodiment.

FIG. 14 illustrates an embodiment in which a wired medical sensor 172 having wireless capabilities may receive communication from the wireless web 16 of medical sensors 14. In the embodiment of FIG. 14, a number of the wireless medical sensors 14 may form a wireless web 16 while attached to a patient 26. In some embodiments, certain sensors 14 may form a separate node 66. Instead of communicating with the patient monitor 12 via a main communication medical sensor 14, the wireless web 16 of medical sensors 14 may instead communicate with the wired medical sensor 172. In some embodiments, the wireless web 16 may determine a main communication medical sensor 14 for communication with the wired medical sensor 172. The wired medical sensor 172 may have essentially the same wireless capabilities as the wireless medical sensors 14, but may maintain a wired connection to the patient monitor 12. In this way, the medical sensors 14 of the wireless web 16 may consume a reduced amount of power due to a reduced transmission distance for wireless communication.

Figure 15:
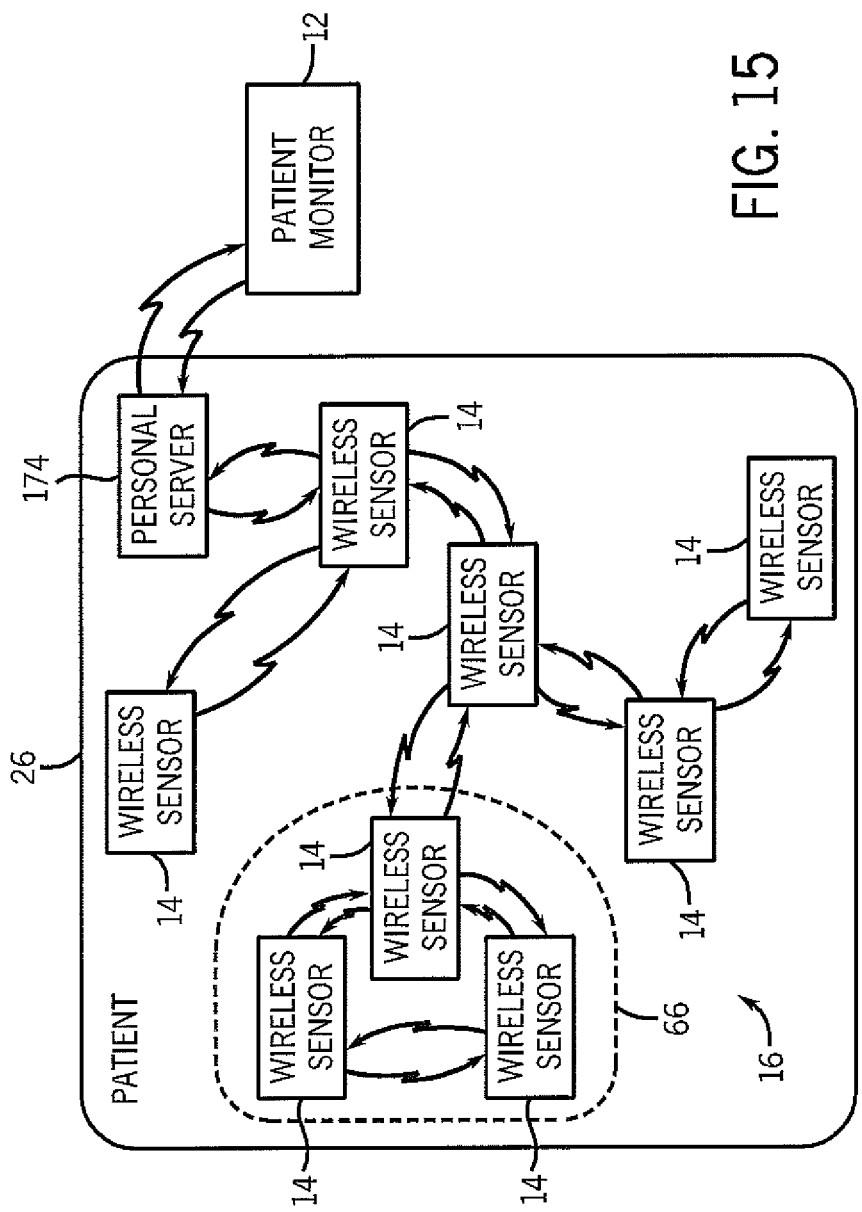
FIG. 15 is a block diagram of a self-assembling wireless web of medical sensors that communicates with a patient monitor via a personal server, in accordance with an embodiment.

FIG. 15 illustrates an embodiment in which a personal server 174 having wireless capabilities may receive communication from the wireless web 16 of medical sensors 14. In the embodiment of FIG. 15, a number of the wireless medical sensors 14 may form a wireless web 16 while attached to a patient 26. In some embodiments, certain sensors 14 may form a separate node 66. Instead of communicating with the patient monitor 12 via a main communication medical sensor 14, the wireless web 16 of medical sensors 14 may instead communicate with the personal server 174. The personal server 174 may facilitate communication between the wireless web 16 and the patient monitor 12.

The personal server 174 may receive low-power communication from the wireless web 16 of medical sensors 14, and may communicate with the patient monitor 12 with higher-power communication. In some embodiments, the wireless web 16 may determine a main communication medical sensor 14 for communication with the personal server 174. Also, in some embodiments, the personal server 174 may communicate with the wireless web 16 using a relatively lower-power wireless protocol, such as those associated with the 802.15.4 IEEE standard, but may communicate with the patient monitor 12 using a relatively higher-power protocol, such as Bluetooth or those protocols associated with the 802.11.x IEEE standard.

Because the personal server 174 may not expend any power obtaining physiological measurements of the patient 26, the personal server 174 may, in some embodiments, receive power by way of the various energy harvesting techniques discussed above. Additionally or alternatively, the personal server 174 may rely primarily on battery power. Also, in some embodiments, the personal server 174 may perform certain processing of the raw physiological measurements obtained by the medical sensors 14 of the wireless web 16. For example, the personal server 174 may process certain of the raw physiological measurements to obtain data of interest related to a specific physiological parameter of the patient 26 (e.g., $SpO_2$, pulse rate, total hemoglobin, and so forth), which may be sent to the patient monitor 12 in lieu of the raw physiological measurements.

Figure 16:
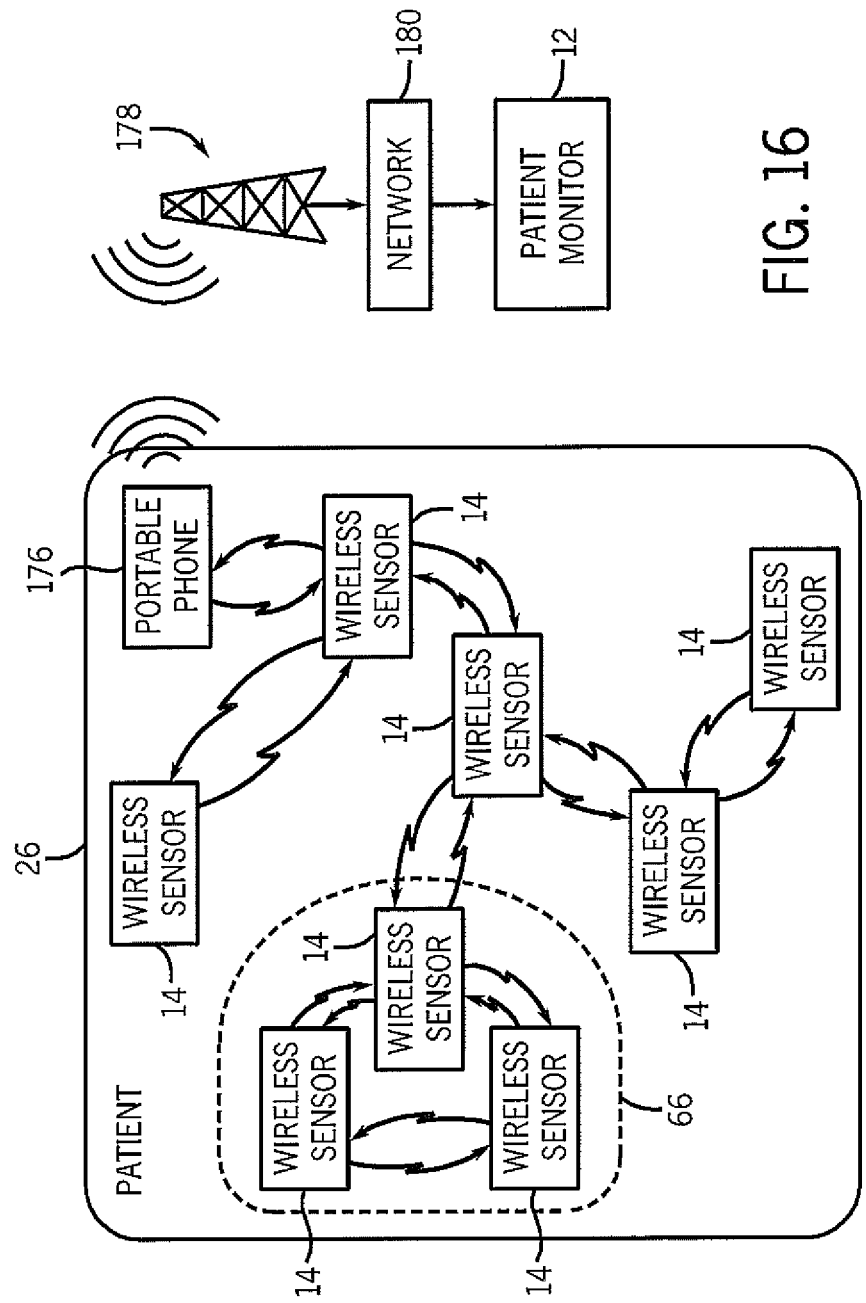
FIG. 16 is a block diagram of a self-assembling wireless web of medical sensors that communicates with a patient monitor via a portable device, such as a portable phone, in accordance with an embodiment.

FIG. 16 illustrates an embodiment in which a portable phone 176 may receive communication from the wireless web 16 of medical sensors 14. In the embodiment of FIG. 16, a number of the wireless medical sensors 14 may form a wireless web 16 while attached to a patient 26. In some embodiments, certain sensors 14 may form a separate node 66. Instead of communicating with the patient monitor 12 via a main communication medical sensor 14, the wireless web 16 of medical sensors 14 may instead communicate with the portable phone 176. The portable phone 176 may facilitate communication between the wireless web 16 and the patient monitor 12 by conveying messages through a cellular network 178 and/or a secondary network 180, such as the Internet. Thus, in at least some embodiments, the portable phone 176 may be understood to be a cellular telephone.

The portable phone 176 may receive low-power communication from the wireless web 16 of medical sensors 14, and may communicate with the patient monitor 12 with higher-power communication. In some embodiments, the wireless web 16 may determine a main communication medical sensor 14 for communication with the portable phone 176. In certain embodiments, the main communication medical sensor 14 may communicate with the wireless web 16 using a relatively lower-power wireless protocol, such as those associated with the 802.15.4 IEEE standard, but may communicate with the portable phone 176 using a relatively higher-power protocol, such as Bluetooth or those protocols associated with the 802.11.x IEEE standards. Also, in some embodiments, the medical sensors 14 of the wireless web 16 may communicate with the portable phone 176 using Bluetooth or similar protocols, and the portable phone 176 may take the place of the main communication medical sensor 14 in the wireless web 16.

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

What is claimed is:

1. A wireless medical sensor comprising:
physiological sensor circuitry configured to obtain a first physiological measurement from a patient;
wireless transceiver circuitry configured to receive a second physiological measurement from at least one other wireless medical sensor at a first update rate and to receive the first physiological measurement from the physiological sensor circuitry, and configured to send the first and second physiological measurements to an external device of a wireless mesh network at a second update rate different than the first update rate; and
control circuitry configured to determine the first update rate and the second update rate based at least in part on a data update rate level factor associated with a physiological status of the patient.

2. The wireless medical sensor of claim 1, wherein the data update rate level factor comprises a value of the first physiological measurement; a historical stability of physiological measurements obtained by the physiological sensor circuitry; a value of the second physiological measurement obtained by the at least one other wireless medical sensor; a historical stability of physiological measurements obtained by the at least one other wireless medical sensor; or any combination thereof.

3. The wireless medical sensor of claim 1, wherein the control circuitry is configured to sample the first physiological measurement, the second physiological measurement, or both, to determine a sampled measurement, and wherein the wireless transceiver circuitry is configured to communicate the sampled measurement to the external device of the wireless mesh network.

4. The wireless medical sensor of claim 1, wherein the control circuitry is configured to determine whether the wireless medical sensor or the at least one other wireless medical sensor is to serve as a main point of communication with the external device of the wireless mesh network based, at least in part, on a communication factor.

5. The wireless medical sensor of claim 4, wherein the communication factor comprises a proximity of the wireless medical sensor to the external device; a button press or switch setting on the wireless medical sensor; an instruction from the external device; or any combination thereof.

6. The wireless medical sensor of claim 4, wherein the communication factor comprises a remaining amount of power of the wireless medical sensor; or a signal quality of the wireless transceiver circuitry; or any combination thereof.

7. The wireless medical sensor of claim 1, comprising an energy harvesting charging device configured to provide power to the wireless medical sensor, wherein the energy harvesting charging device is configured to harvest piezoelectric energy; inductive energy; or thermoelectric energy; or any combination thereof.

8. The wireless medical sensor of claim 1, wherein the data update rate level factor comprises a current location of a clinician relative to the patient; the current location of the patient relative to the external device; an initialization status of the wireless medical sensor; or a remaining amount of power of the wireless medical sensor; or any combination thereof.

9. The wireless medical sensor of claim 1, wherein the at least one other wireless medical sensor does not wirelessly communicate with the external device.

10. The wireless medical sensor of claim 1, comprising a memory device configured to store the second physiological measurement or queue the second physiological measurement for transmission to the external device.

11. The wireless medical sensor of claim 1, wherein the control circuitry is configured to utilize one or more communication factors to determine whether the wireless medical sensor or the at least one other wireless medical sensor is to serve as a main point of communication with the external device of the wireless mesh network, and the control circuitry is configured to select the one or more communication factors based on the physiological status of the patient.

12. The wireless medical sensor of claim 1, wherein the control circuitry is configured to determine a first value for the second data update rate when at least one of the first and second physiological measurements indicates that the patient is in a healthy condition and to determine a second value for the second update rate when the at least one of the first and second physiological measurements indicates that the patient is in an unhealthy condition, and wherein the first value is less than the second value.

13. A method comprising:
activating a first wireless medical sensor following a period of inactivity of the first wireless medical sensor, wherein the first wireless medical sensor is communicatively coupled to a wireless mesh network comprising at least a second wireless medical sensor, and wherein the period of inactivity of the first wireless medical sensor is synchronized with a period of activity of the second wireless medical sensor;
obtaining a first physiological measurement from a patient using the first wireless medical sensor;
obtaining a second physiological measurement from the patient using the second wireless medical sensor;
sending, via the second wireless medical sensor, the second physiological measurement to the first wireless medical sensor at a first update rate;
receiving, via the first wireless medical sensor, the second physiological measurement from the second wireless medical sensor at the first update rate;
communicating the first and the second physiological measurements from the first wireless medical sensor to an external device at a second update rate different than the first update rate, wherein the first update rate and the second update rate are based at least in part on a physiological status of the patient, and wherein a length of the period of inactivity of the first wireless medical sensor is based at least in part on the second update rate; and
deactivating the first wireless medical sensor.

14. The method of claim 13, comprising:
assessing one or more data update rate factors of the first wireless medical sensor, wherein the one or more data update rate factors comprise a physiological status of the patient and one or more of a presence or absence of a clinician relative to the patient, a current location of the patient within a medical facility, the current location of the patient relative to a patient monitor, a movement of the patient, an initialization status of the wireless medical sensor, or an amount of power remaining in the wireless medical sensor, or a combination thereof; and
determining the first update rate and the second update rate for the first wireless medical sensor based on the one or more data update rate factors.

15. The method of claim 14, comprising communicating the determined first update rate to at least one other wireless medical sensor of the wireless mesh network.

16. The method of claim 13, wherein the second update rate comprises a first value when physiological measurements obtained by at least one of the first wireless medical sensor and the second wireless medical sensor indicate that the patient is in a healthy condition and comprises a second value, greater than the first value, when the physiological measurements obtained by at least one of the first wireless medical sensor and the second wireless medical sensor indicate that the patient is in an unhealthy condition.

17. A patient monitor comprising:
a wireless transceiver configured to join a wireless mesh network of medical sensors, receive physiological measurements from a patient from the wireless mesh network of medical sensors at a first rate, and transmit to the wireless mesh network of medical sensors instructions to operate at a second rate different than the first rate to collect the physiological measurements from the patient; and
data processing circuitry configured to determine a physiological parameter of the patient based at least in part on the received physiological measurements of the patient and determine the first rate and the second rate based at least in part on a data update rate level factor, wherein the data update rate level factor comprises a current location of the patient within a medical facility, the current location of the patient relative to the patient monitor, the current location of the patient relative to a clinician, a movement of the patient, or a combination thereof.

18. The patient monitor of claim 17, wherein the data update rate level factor further comprises a value of one of the physiological measurements; a historical stability of the physiological measurements; a button press or switch setting on one of the medical sensors of the wireless mesh network of medical sensors; a button press or switch setting on the patient monitor; an initialization status of the wireless mesh network of medical sensors; a remaining amount of power of one of the medical sensors of the wireless mesh network of medical sensors; or a data update rate level determined by one of the medical sensors of the wireless mesh network of medical sensors; or any combination thereof.

19. The patient monitor of claim 17, wherein the data update rate level factor is determined and communicated to the wireless mesh network of medical sensors via the patient monitor.

20. The patient monitor of claim 17, wherein the data update rate level factor further comprises a historical stability of the physiological measurements.

21. A system comprising:
two or more medical sensors configured to obtain physiological measurements from a patient and communicatively couple with a wireless mesh network and a bridging device, wherein the two or more medical sensors are configured to provide the bridging device with the physiological measurements at a first data update rate that is based at least in part on a physiological status of the patient and a parameter of the two or more medical sensors; and
a patient monitor configured to communicatively couple to the bridging device, wherein the patient monitor is configured to receive from the bridging device the physiological measurements at a second data update rate different than the first data update rate, and wherein the patient monitor is configured to determine one or more physiological parameters of the patient based at least in part on the physiological measurements, and wherein the bridging device is configured to separately communicate with the patient monitor and the wireless mesh network;

wherein the two or more medical sensors, the bridging device, or the patient monitor, or a combination thereof, are configured to determine the first data update rate and the second data update rate based at least in part on the physiological status of the patient and the parameter of the two or more medical sensors.

22. The system of claim 21, wherein the bridging device comprises a main communication medical sensor and wherein the patient monitor is configured to communicate wirelessly with the main communication medical sensor.

23. The system of claim 21, wherein the bridging device comprises a local transceiver configured to facilitate communication between the patient monitor and the wireless mesh network by communicating wirelessly with the wireless mesh network and by communicating by wire with the patient monitor.

24. The system of claim 21, wherein the bridging device comprises a wired medical sensor configured to facilitate communication between the patient monitor and the wireless mesh network by communicating wirelessly with the wireless mesh network and by communicating by wire with the patient monitor.

25. The system of claim 21, wherein the bridging device comprises a personal server configured to facilitate communication between the patient monitor and the wireless mesh network by separately communicating wirelessly with the wireless mesh network and the patient monitor.

26. The system of claim 25, wherein the personal server is configured to communicate wirelessly with the wireless mesh network using a first protocol and communicating wirelessly with the patient monitor using a second protocol.

27. The system of claim 21, wherein the bridging device comprises a portable phone configured to facilitate communication between the patient monitor and the wireless mesh network by separately communicating wirelessly with the wireless mesh network and communicating wirelessly with the patient monitor via a cellular network.

28. The system of claim 21, wherein the physiological measurements are indicative of the physiological status of the patient, and wherein the two or more medical sensors, the bridging device, or the patient monitor, or a combination thereof, are configured to determine a first value for the second data update rate when the physiological measurements are within respective predetermined acceptable ranges and to determine a second value, higher than the first value, for the second data update rate in response to at least one of the physiological measurements being outside of a respective predetermined acceptable range.

29. The system of claim 21, wherein the parameter of the two or more medical sensors comprises an initialization status of the two or more medical sensors, or an amount of power remaining for the two or more medical sensors, or a combination thereof.

30. A method comprising:

providing a first wireless medical sensor configured to form a wireless web with a second wireless medical sensor, wherein the first wireless medical sensor is configured to operate at a first data update rate level based at least in part on a data update rate level factor comprising a current location of a patient within a medical facility, the current location of the patient relative to a patient monitor, the current location of the patient relative to a clinician, a movement of the patient, or a combination thereof, and wherein the first wireless medical sensor is configured to deactivate for a period of time based at least in part on the data update rate level factor;

providing the second wireless medical sensor, wherein the second wireless medical sensor is configured to form the wireless web with the first wireless medical sensor and wherein the second wireless medical sensor is configured to operate at the first data update rate level, and wherein the second wireless medical sensor is configured to activate for the period of time that the first wireless medical sensor is deactivated; and providing the patient monitor configured to receive physiological measurements from the wireless web at a second data update rate level different than the first data update rate level, wherein the second update rate is based at least in part on the data update rate level factor.

31. The method of claim 30, wherein the data update rate level factor of the first wireless medical sensor further comprises an initialization status of the first wireless medical sensor, or a power status of the first wireless medical sensor, or a combination thereof.

* * * * *